(12) United States Patent
Manzo et al.

(10) Patent No.: US 12,262,938 B2
(45) Date of Patent: Apr. 1, 2025

(54) MEDICAL INSTRUMENT ELECTRICALLY ENERGIZED USING DRIVE CABLES

(71) Applicant: Intuitive Surgical Operations, Inc., Sunnyvale, CA (US)

(72) Inventors: Scott E. Manzo, Shelton, CT (US); William A. Burbank, Sandy Hook, CT (US); Richard D. Gresham, Guilford, CT (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 499 days.

(21) Appl. No.: 17/496,432

(22) Filed: Oct. 7, 2021

(65) Prior Publication Data
US 2022/0022943 A1 Jan. 27, 2022

Related U.S. Application Data

(60) Continuation of application No. 15/855,561, filed on Dec. 27, 2017, now Pat. No. 11,357,566, which is a
(Continued)

(51) Int. Cl.
*A61B 18/14* (2006.01)
*A61B 34/00* (2016.01)
(Continued)

(52) U.S. Cl.
CPC .......... *A61B 18/1445* (2013.01); *A61B 34/71* (2016.02); *A61B 2017/003* (2013.01);
(Continued)

(58) Field of Classification Search
CPC ................ A61B 17/32; A61B 18/1445; A61B 2017/003; A61B 2017/00318;
(Continued)

(56) References Cited

U.S. PATENT DOCUMENTS 4,341,144 A 7/1982 Milne
5,325,845 A 7/1994 Adair
(Continued)

FOREIGN PATENT DOCUMENTS

CA 2853431 A1 5/2013
CN 102458551 A 5/2012
(Continued)

OTHER PUBLICATIONS

Non-Final Office Action mailed Aug. 5, 2021 for U.S. Appl. No. 16/205,642, filed Nov. 30, 2018, 7 pages.
(Continued)

*Primary Examiner* — Quynh-Nhu H. Vu

(57) ABSTRACT

An electrically energized medical instrument uses one or more drive cables to both actuate mechanical components of a wrist mechanism or an effector and to electrically energize the effector. Electrical isolation can be achieved using an insulating main tube through which drive cables extend from a backend mechanism to the effector, an insulating end cover that leaves only the desired portions of the effector exposed, and one or more seals to prevent electrically conductive liquid from entering the main tube. Component count and cost may be further reduced using a pair of pulleys that are shared by four drive cables.

13 Claims, 10 Drawing Sheets

Related U.S. Application Data continuation of application No. 14/933,875, filed on Nov. 5, 2015, now abandoned, which is a division of application No. 12/173,938, filed on Jul. 16, 2008, now Pat. No. 9,204,923.

(51) Int. Cl.

| | | |
|---|---|---|
| A61B 17/00 | (2006.01) | |
| A61B 17/29 | (2006.01) | |
| A61B 17/32 | (2006.01) | |
| A61B 18/00 | (2006.01) | |
| A61B 34/30 | (2016.01) | |

(52) U.S. Cl.
CPC ........... *A61B 2017/00323* (2013.01); *A61B 2017/2927* (2013.01); *A61B 2017/2945* (2013.01); *A61B 17/32* (2013.01); *A61B 2018/00345* (2013.01); *A61B 2018/00404* (2013.01); *A61B 2018/00595* (2013.01); *A61B 2018/00601* (2013.01); *A61B 2018/00619* (2013.01); *A61B 2018/1432* (2013.01); *A61B 2018/146* (2013.01); *A61B 34/30* (2016.02); *A61B 2034/305* (2016.02)

(58) Field of Classification Search
CPC ........... A61B 2017/00323; A61B 2017/00327; A61B 2017/2927; A61B 2017/2929; A61B 2017/2945; A61B 2018/146; A61B 2034/305; A61B 34/30; A61B 34/71
See application file for complete search history.

(56) References Cited

U.S. PATENT DOCUMENTS

| | | | |
|---|---|---|---|
| 5,395,369 A | 3/1995 | McBrayer et al. | |
| 5,396,900 A | 3/1995 | Slater et al. | |
| 5,482,054 A | 1/1996 | Slater et al. | |
| 5,496,317 A | 3/1996 | Goble et al. | |
| 5,496,347 A | 3/1996 | Hashiguchi et al. | |
| 5,624,398 A | 4/1997 | Smith et al. | |
| 5,715,832 A | 2/1998 | Koblish et al. | |
| 5,784,542 A | 7/1998 | Ohm et al. | |
| 5,792,135 A | 8/1998 | Madhani et al. | |
| 5,792,165 A | 8/1998 | Klieman et al. | |
| 5,807,377 A | 9/1998 | Madhani et al. | |
| 5,855,583 A | 1/1999 | Wang et al. | |
| 5,876,325 A | 3/1999 | Mizuno et al. | |
| 5,899,914 A | 5/1999 | Zirps et al. | |
| 5,916,146 A | 6/1999 | Allotta et al. | |
| 6,007,550 A | 12/1999 | Wang et al. | |
| 6,197,017 B1 | 3/2001 | Brock et al. | |
| 6,206,903 B1 | 3/2001 | Ramans | |
| 6,237,604 B1 | 5/2001 | Burnside et al. | |
| 6,273,860 B1 | 8/2001 | Kostylev et al. | |
| 6,309,397 B1 | 10/2001 | Julian et al. | |
| 6,331,181 B1 | 12/2001 | Tierney et al. | |
| 6,371,952 B1 | 4/2002 | Madhani et al. | |
| 6,371,956 B1 | 4/2002 | Wilson et al. | |
| 6,394,998 B1 * | 5/2002 | Wallace | A61B 34/35 901/29 |
| 6,398,726 B1 | 6/2002 | Ramans et al. | |
| 6,464,701 B1 | 10/2002 | Hooven et al. | |
| 6,491,626 B1 | 12/2002 | Stone et al. | |
| 6,491,691 B1 | 12/2002 | Morley et al. | |
| 6,491,701 B2 | 12/2002 | Tierney et al. | |
| 6,554,844 B2 * | 4/2003 | Lee | A61B 5/0084 606/1 |
| 6,623,482 B2 | 9/2003 | Pendekanti et al. | |
| 6,676,684 B1 * | 1/2004 | Morley | A61B 34/30 606/205 |
| 6,685,698 B2 | 2/2004 | Morley et al. | |
| 6,733,495 B1 | 5/2004 | Bek et al. | |
| 6,767,349 B2 | 7/2004 | Ouchi | |
| 6,817,974 B2 | 11/2004 | Cooper et al. | |
| 6,840,938 B1 | 1/2005 | Morley et al. | |
| 6,843,793 B2 | 1/2005 | Brock et al. | |
| 6,949,106 B2 | 9/2005 | Brock et al. | |
| 6,964,662 B2 | 11/2005 | Kidooka | |
| 6,969,385 B2 | 11/2005 | Moreyra | |
| 6,991,627 B2 | 1/2006 | Madhani et al. | |
| 6,994,708 B2 | 2/2006 | Manzo | |
| 7,083,571 B2 | 8/2006 | Wang et al. | |
| 7,090,683 B2 | 8/2006 | Brock et al. | |
| 7,125,403 B2 | 10/2006 | Julian et al. | |
| 7,147,650 B2 | 12/2006 | Lee | |
| 7,169,141 B2 | 1/2007 | Brock et al. | |
| 7,214,230 B2 | 5/2007 | Brock et al. | |
| 7,320,700 B2 | 1/2008 | Cooper et al. | |
| 7,338,513 B2 | 3/2008 | Lee et al. | |
| 7,354,439 B2 | 4/2008 | Kidooka | |
| 7,371,210 B2 | 5/2008 | Brock et al. | |
| 7,422,592 B2 | 9/2008 | Morley et al. | |
| 7,582,055 B2 | 9/2009 | Komiya et al. | |
| 7,608,083 B2 | 10/2009 | Lee et al. | |
| 7,648,519 B2 | 1/2010 | Lee et al. | |
| 7,682,307 B2 | 3/2010 | Danitz et al. | |
| 7,699,835 B2 | 4/2010 | Lee et al. | |
| 7,785,252 B2 | 8/2010 | Danitz et al. | |
| 7,824,401 B2 | 11/2010 | Manzo et al. | |
| 7,935,130 B2 | 5/2011 | Williams | |
| 8,142,421 B2 | 3/2012 | Cooper et al. | |
| 8,142,447 B2 | 3/2012 | Cooper et al. | |
| 8,245,595 B2 | 8/2012 | Milenkovic | |
| 8,347,757 B2 | 1/2013 | Duval | |
| 8,479,969 B2 | 7/2013 | Shelton, IV | |
| 8,540,748 B2 | 9/2013 | Murphy et al. | |
| 8,551,115 B2 | 10/2013 | Steger et al. | |
| 8,597,182 B2 | 12/2013 | Stein et al. | |
| 8,602,288 B2 | 12/2013 | Shelton, IV et al. | |
| 8,771,270 B2 | 7/2014 | Burbank | |
| 8,800,838 B2 | 8/2014 | Shelton, IV | |
| 8,821,480 B2 | 9/2014 | Burbank | |
| 9,028,494 B2 | 5/2015 | Shelton, IV et al. | |
| 9,078,684 B2 | 7/2015 | Williams | |
| 9,186,221 B2 | 11/2015 | Burbank | |
| 9,204,923 B2 | 12/2015 | Manzo et al. | |
| 9,232,979 B2 | 1/2016 | Parihar et al. | |
| 9,259,275 B2 | 2/2016 | Burbank | |
| 9,339,341 B2 | 5/2016 | Cooper | |
| 9,358,031 B2 | 6/2016 | Manzo | |
| 9,533,122 B2 | 1/2017 | Weitzner et al. | |
| 9,782,214 B2 | 10/2017 | Houser et al. | |
| 10,130,366 B2 | 11/2018 | Shelton, IV et al. | |
| 10,201,365 B2 | 2/2019 | Boudreaux et al. | |
| 10,285,763 B2 | 5/2019 | Vale et al. | |
| 10,335,177 B2 | 7/2019 | Steger | |
| 10,499,891 B2 | 12/2019 | Chaplin et al. | |
| 10,524,870 B2 | 1/2020 | Saraliev et al. | |
| 10,624,703 B2 | 4/2020 | Chaplin et al. | |
| 10,682,141 B2 | 6/2020 | Moore et al. | |
| 11,272,977 B2 | 3/2022 | Manzo et al. | |
| 11,717,364 B2 | 8/2023 | Penny et al. | |
| 2001/0025134 A1 | 9/2001 | Bon et al. | |
| 2002/0111621 A1 | 8/2002 | Wallace et al. | |
| 2004/0019352 A1 | 1/2004 | Kidooka | |
| 2004/0162557 A1 | 8/2004 | Tetzlaff et al. | |
| 2004/0260198 A1 | 12/2004 | Rothberg et al. | |
| 2004/0266574 A1 | 12/2004 | Jinno et al. | |
| 2005/0187547 A1 | 8/2005 | Sugi | |
| 2005/0240178 A1 | 10/2005 | Morley et al. | |
| 2006/0074415 A1 | 4/2006 | Scott et al. | |
| 2006/0131908 A1 | 6/2006 | Tadano | |
| 2006/0190034 A1 | 8/2006 | Nishizawa et al. | |
| 2007/0158385 A1 | 7/2007 | Hueil et al. | |
| 2007/0208375 A1 | 9/2007 | Nishizawa et al. | |
| 2007/0246508 A1 | 10/2007 | Green | |
| 2008/0046122 A1 | 2/2008 | Manzo et al. | |
| 2008/0065102 A1 | 3/2008 | Cooper | |
| 2008/0065105 A1 | 3/2008 | Larkin et al. | |
| 2008/0125794 A1 | 5/2008 | Brock et al. | |
| 2008/0132893 A1 | 6/2008 | D'Amelio et al. | |
| 2008/0167651 A1 | 7/2008 | Tetzlaff et al. | |

(56) References Cited

U.S. PATENT DOCUMENTS

| | | |
|---|---|---|
| 2008/0196533 A1 | 8/2008 | Bergamasco et al. |
| 2008/0255421 A1 | 10/2008 | Hegeman et al. |
| 2009/0088774 A1 | 4/2009 | Swarup et al. |
| 2009/0131975 A1 | 5/2009 | Ahlberg et al. |
| 2009/0171348 A1 | 7/2009 | Guo et al. |
| 2009/0198272 A1 | 8/2009 | Kerver et al. |
| 2009/0209960 A1 | 8/2009 | Chojin |
| 2009/0326530 A1 | 12/2009 | Orban, III et al. |
| 2010/0030238 A1 | 2/2010 | Viola et al. |
| 2010/0198218 A1 | 8/2010 | Manzo |
| 2010/0198253 A1 | 8/2010 | Jinno et al. |
| 2011/0071543 A1 | 3/2011 | Prisco et al. |
| 2011/0152879 A1 | 6/2011 | Williams |
| 2011/0295269 A1 | 12/2011 | Swensgard et al. |
| 2011/0295270 A1 | 12/2011 | Giordano et al. |
| 2011/0301599 A1 | 12/2011 | Roy et al. |
| 2013/0123783 A1 | 5/2013 | Marczyk et al. |
| 2013/0304084 A1 | 11/2013 | Beira et al. |
| 2013/0345718 A1 | 12/2013 | Crawford et al. |
| 2014/0005662 A1 | 1/2014 | Shelton, IV |
| 2014/0005678 A1 | 1/2014 | Shelton, IV et al. |
| 2014/0073856 A1 | 3/2014 | Stein et al. |
| 2014/0257331 A1 | 9/2014 | Kim et al. |
| 2014/0257333 A1 | 9/2014 | Blumenkranz |
| 2014/0276956 A1 | 9/2014 | Crainich et al. |
| 2015/0157355 A1 | 6/2015 | Price et al. |
| 2015/0280384 A1 | 10/2015 | Leimbach et al. |
| 2015/0374447 A1 | 12/2015 | Blumenkranz et al. |
| 2016/0051318 A1 | 2/2016 | Manzo et al. |
| 2016/0058443 A1 | 3/2016 | Yates et al. |
| 2016/0143688 A1 | 5/2016 | Orban, III et al. |
| 2016/0296219 A1 | 10/2016 | Srivastava et al. |
| 2016/0361123 A1 | 12/2016 | Hares et al. |
| 2017/0007242 A1 | 1/2017 | Shelton, IV et al. |
| 2017/0215944 A1 | 8/2017 | Keffeler |
| 2017/0265954 A1 | 9/2017 | Burbank et al. |
| 2018/0116708 A1 | 5/2018 | Manzo et al. |
| 2018/0200895 A1 | 7/2018 | Kan |
| 2019/0069966 A1 | 3/2019 | Petersen et al. |
| 2019/0090940 A1 | 3/2019 | Manzo et al. |
| 2019/0094084 A1 | 3/2019 | Swinehart et al. |
| 2019/0167368 A1 | 6/2019 | Yoshii |
| 2019/0201018 A1 | 7/2019 | Shelton, IV et al. |
| 2019/0239877 A1 | 8/2019 | Ragosta et al. |
| 2019/0239967 A1 | 8/2019 | Ragosta et al. |
| 2019/0290310 A1 | 9/2019 | Klein |
| 2019/0328467 A1 | 10/2019 | Waterbury et al. |
| 2019/0336228 A1 | 11/2019 | Blumenkranz et al. |
| 2020/0129226 A1 | 4/2020 | Manzo et al. |
| 2020/0173525 A1 | 6/2020 | Cooper et al. |
| 2021/0022819 A1 | 1/2021 | Duque et al. |
| 2021/0196413 A1 | 7/2021 | Inque |
| 2021/0290322 A1 | 9/2021 | Traina |
| 2021/0322118 A1 | 10/2021 | Donlon et al. |
| 2022/0354474 A1 | 11/2022 | Ratia et al. |
| 2024/0341887 A1 | 10/2024 | Sadaka |

FOREIGN PATENT DOCUMENTS

| | | |
|---|---|---|
| CN | 104116547 A | 10/2014 |
| CN | 106714721 A | 5/2017 |
| CN | 113262051 A | 8/2021 |
| EP | 1151723 A2 | 11/2001 |
| EP | 1847289 A2 | 10/2007 |
| EP | 2362285 A2 | 8/2011 |
| EP | 2548529 A1 | 1/2013 |
| EP | 2783643 A1 | 10/2014 |
| EP | 3100666 A1 | 12/2016 |
| FR | 3016543 A1 | 7/2015 |
| GB | 191012759 A | 3/1911 |
| GB | 2590881 A | 7/2021 |
| JP | 2002503131 A | 1/2002 |
| JP | 2006061364 A | 3/2006 |
| JP | 2010022696 A | 2/2010 |
| JP | 2013017542 A | 1/2013 |
| KR | 100778387 B1 | 11/2007 |
| WO | WO-02080783 A1 | 10/2002 |
| WO | WO-2010081050 A1 | 7/2010 |
| WO | WO-2011097095 A1 | 8/2011 |
| WO | WO-2013181522 A1 | 12/2013 |
| WO | WO-2014151952 A1 | 9/2014 |
| WO | WO-2016025132 A1 | 2/2016 |
| WO | WO-2017064306 A1 | 4/2017 |
| WO | WO-2019199827 A1 | 10/2019 |
| WO | WO-2023177565 A1 | 9/2023 |

OTHER PUBLICATIONS

Non-Final Office Action mailed Feb. 5, 2018 for U.S. Appl. No. 14/933,875, filed Nov. 5, 2015, 9 pages.

Notice of Allowance mailed Feb. 22, 2021 for KR Application No. 10-2020-7013101 filed on Jul. 16, 2009, 3 pages.

Office Action for U.S. Appl. No. 15/855,561 mailed on Oct. 28, 2021, 17 pages.

PCT/US09/50671 International Search Report and Written Opinion of the International Searching Authority, mailed Jan. 21, 2010. 19 pages.

PCT/US09/50671 Invitation to Pay Additional Fees and Partial International Search Report, mailed Nov. 6, 2009, 6 pages.

PCT/US09/50678 International Search Report and Written Opinion of the International Searching Authority, mailed Jan. 12, 2010, 9 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for U.S. Appl. No. 16/727,468, mailed Apr. 15, 2022, 13 pages.

* cited by examiner

MEDICAL INSTRUMENT ELECTRICALLY ENERGIZED USING DRIVE CABLES

CROSS-REFERENCE TO RELATED APPLICATIONS

This patent application is a continuation U.S. patent application Ser. No. 15/855,561, filed Dec. 27, 2017, which is a continuation of U.S. patent application Ser. No. 14/933,875, filed Nov. 5, 2015, which is a divisional of U.S. patent application Ser. No. 12/173,938, filed Jul. 16, 2008 (now U.S. Pat. No. 9,204,923), which is related to and incorporates by reference U.S. patent application Ser. No. 12/173,934, entitled "Four-Cable Wrist with Solid Surface Cable Channels," each of which is incorporated herein by reference in its entirety.

BACKGROUND

Minimally invasive medical procedures generally employ small diameter instruments that can be inserted directly or through a cannula in a small incision or natural orifice of a patient. Producing small diameter medical instruments that implement the clinically desired functions for minimally invasive procedures can be challenging. For example, many instruments require a small-diameter wrist mechanism that is able to position and manipulate an end effector at the distal end of the instrument. Such wrist mechanisms commonly employ two cables per rotation axis available in the wrist, so that a wrist mechanism providing pitch, yaw, and grip control commonly uses six cables. All of the cables must be routed through the wrist mechanism and back through a small-diameter tube to a transmission, sometimes referred to herein as a backend mechanism. The backend mechanism moves the drive cables as needed to operate the wrist mechanism. Further, some medical instruments have end effectors that require electrical energy, for example, for clinical functions such as desiccation, hemostasis, cutting, dissection, fulguration, incisions, tissue destruction, cauterizing, and vessel sealing. Accordingly, one or more conductors must be routed to the portion of an end effector to be energized, while other portions of the instrument must be insulated from the electrical energy to avoid unintended burning of the patient or a user of the instrument. Fitting all the components of the wrist mechanism, drive cables, and conductive wires into a small diameter, for example, less than about 10 mm, can be difficult.

Minimally invasive medical instruments with lower part counts are desired to facilitate miniaturization of the instrument and to reduce instrument costs.

SUMMARY

In accordance with an aspect of the invention, an electrically energized medical instrument uses one or more drive cables both to actuate mechanical components of a wrist mechanism or an end effector and to electrically energize the end effector. Electrical isolation can be achieved using an insulating main tube through which drive cables extend from a backend mechanism to an end effector, an insulating end cover that leaves only the desired portions of the end effector exposed, and one or more seals to prevent electrically conductive liquid from entering the main tube. A reduction in the number of components achieved by some embodiments of the invention can result in a cost savings in a reusable instrument or permit creation of a single-use instrument that is cost competitive with reusable instruments on a per use basis.

One specific embodiment of the invention is a medical instrument including a main tube, an end effector, a cable, and a backend mechanism. The end effector is attached to a distal end of the main tube and contains an electrically conductive component such as a scissors blade. The cable extends the length of the main tube and is coupled to the end effector so that actuation of the end effector involves movement of the cable. The cable is also electrically conductive. The backend mechanism is coupled to a proximal end of the main tube and includes a mechanical system and an electrical system. The mechanical system is coupled to the cable and is operable to move the cable for the actuation of the end effector. The electrical system is connected to the cable for application of an electrical signal that energizes the electrically conductive component of the end effector. The energized end effector can then be used for a clinical function such as destroying or cauterizing tissue.

Another embodiment of the invention is a method for operating a medical instrument. The method includes: actuating an end effector on a distal end of a main tube through movement of one or more cables that are attached to the end effector; and electrically energizing the end effector by applying an electrical signal that one or more of the cables conducts through the main tube to the end effector.

Yet another embodiment of the invention is a medical instrument including a clevis, a pair of pulleys, a pair of jaws, and four drive cables. The clevis and the pulleys are rotatably mounted on a first pin. The jaws are rotatably mounted on a second pin that is in the clevis. A first and a second of the cables attach to one jaw and respectively ride on the first and second pulleys when the clevis is in a first position. A third and a fourth of the cables attach to the other jaw and also ride on the first and second pulleys, respectively, when the clevis is in the first position. Having four cables share two pulleys decreases the part count and the cost of the instrument. The pulleys reduce cable friction because for many motions of the instrument (e.g., change of the pitch angle or closing/opening of the jaws) the rotation of each pulley matches the movement of both cables that ride on the pulley. For other motions of the instrument, a cable may slide or slip on a pulley when the motions of both cables cannot simultaneously be matched to the rotation of the pulley. However, the pulley will generally rotate with whichever of the associated cables exerts greater force on the pulley, e.g., has the larger wrap angle and/or tension, so that the total cable friction can be reduced even when a cable is required to slide against the surface of a pulley.

BRIEF DESCRIPTION OF THE DRAWINGS

Use of the same reference symbols in different figures indicates similar or identical items.

DETAILED DESCRIPTION

In accordance with an aspect of the invention, a robotically actuated, electrically energized instrument can use one or more actuating or drive cables for electrical power. One specific embodiment of the invention is a low cost, wristed, electrically energized, scissor instrument that can be actuated using a robotic control system such as the da Vinci system available from Intuitive Surgical, Inc. Using drive cables for electrical energy can reduce the number of component parts, which can result in cost reduction and can facilitate miniaturization of instruments for minimally invasive medical procedures. An additional reduction in the part count and costs can be achieved by routing multiple cables around the same pulley in the wrist of the instrument.

Figure 1:
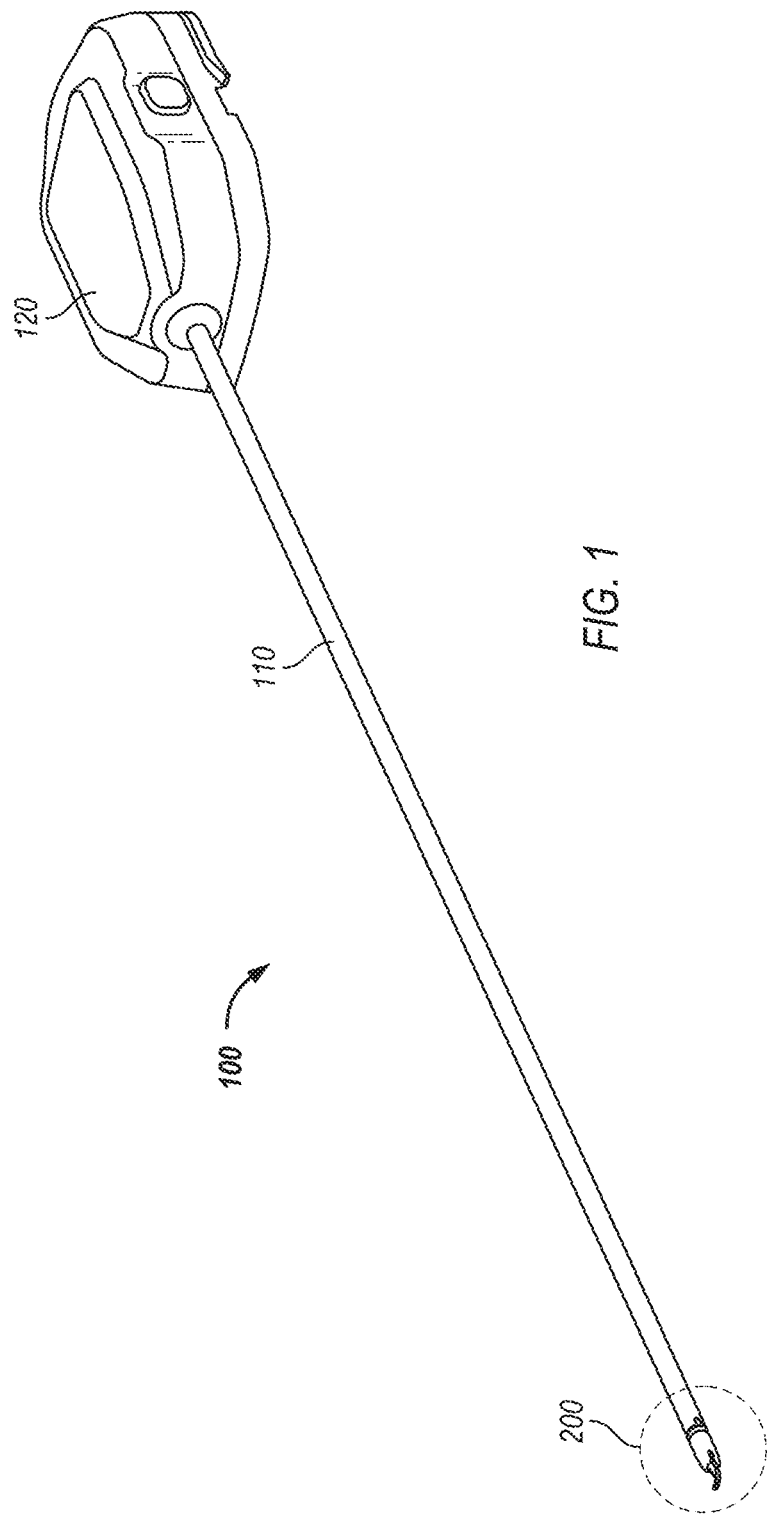
FIG. 1 shows a medical instrument that operates as an energized end effector in accordance with an embodiment of the invention.

FIG. 1 shows a configuration for a medical instrument 100 in accordance with an exemplary embodiment of the invention. Medical instrument 100 includes an end effector 200 at a distal end of a main tube 110 that extends from a transmission or backend mechanism 120. During a minimally invasive medical procedure, end effector 200 and the distal end of main tube 110 can be directly inserted or inserted through a cannula or other guide that may be inserted through a small incision or a natural orifice of a patient undergoing the medical procedure. Accordingly, the diameter of end effector 200 and main tube 110 and the length of main tube 110 may be selected according to the size of the cannula with which the instrument will be used. In an exemplary embodiment, end effector 200 and main tube 110 are about 5 mm or about 8 mm in diameter to match the sizes of some existing cannula systems, and the length of main tube 110 can be about 460 mm.

Main tube 110 is hollow to contain drive cables that run from backend mechanism 120 to end effector 200. In accordance with an aspect of the current invention, main tube 110 is made of an electrically insulating material such as a plastic or polymer material to isolate the drive cables, which may be electrically energized, from the surrounding environment. Main tube 110 may be rigid or flexible. A flexible main tube 100 would be used, for example, for insertion through an endoscope or other guide or cannula that follows a natural lumen or otherwise curved path. However, many common types of minimally invasive medical procedures such as laparoscopic surgery employ straight cannulas for insertion and removal of instruments, permitting use of a rigid main tube 110. A rigid main tube 110 can provide a solid base for use of end effector 200 during a medical procedure. A rigid/straight main tube 110 also permits portions of drive cables extending through main tube 110 to be structures such as rods or tubes (e.g., hypotubes) that may provide better immunity to stretching or be less expensive.

Backend mechanism 120 can contain an electrical system for energizing end effector 200 and a mechanical system that acts as a transmission and provides a mechanical interface between the drive cables extending through main tube 110 and a control system (not shown). In an exemplary embodiment of the invention, the control system is the da Vinci system available from Intuitive Surgical, Inc. The control system contains drive motors under the control of a processing system, software, and input from a user interface. In general, backend mechanism 120 is shaped to be fitted in a docking port or elsewhere onto the control system so that motor driven axes of the control system can operate end effector 200 to produce desired movements, e.g., changes of the pitch, yaw, and grip of end effector 200.

Figure 2A:
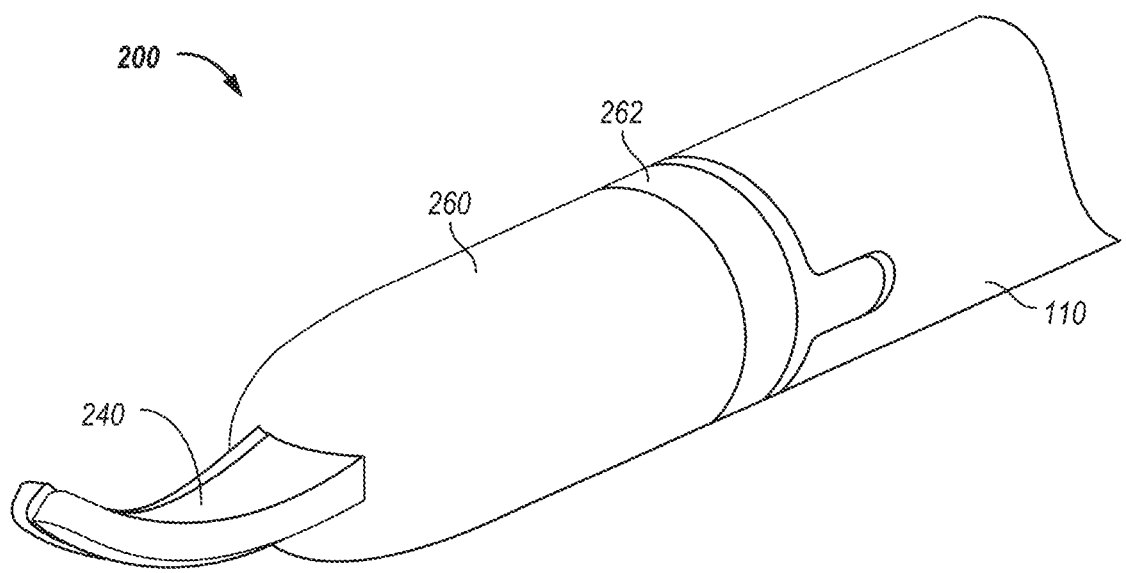
FIGS. 2A and 2B respectively show closed and open configurations of scissors in an end effector suitable for the medical instrument of FIG. 1.

FIG. 2A shows an embodiment in which end effector 200 contains scissors 240. Scissors 240 can be electrically energized with an AC signal. For example, the AC signals may use a voltage of 100 volts up to 10,000 volts or more and a frequency above 100 kHz and typically between about 350 kHz and 4 MHz. Such AC signals are known in the art for performing clinical functions such as desiccation, hemostasis, cutting, dissection, fulguration, incisions, tissue destruction, cauterizing, and vessel sealing without shocking a patient. An insulating cover 260 shown in FIG. 2A covers most of end effector 200 so that only the blades of scissors 240 are exposed. During a medical procedure, scissors 240 can be energized with the high voltage AC signal when a contact pad on the patient is grounded or energized with an opposite polarity AC signal. Since only the blades of scissors 240 expose electricity to the patient, an electrical current flows only from the blades through tissue adjacent to the blades when scissors 240 are electrically energized. The concentration of electrical current can be used to destroy tissue and/or cauterize tissue during cutting with or other use of scissors 240. The contact pad on the patient's body is designed to make a wide area electrical connection to spread the current sufficiently to avoid tissue damage or burning at the body contact or anywhere away from the blades of scissors 240.

Cover 260 can be made of rubber, silicone, or another flexible insulating material and is attached to main tube 110 by a compression clip 262 or alternatively by an elastic ring, a heat shrinkable ring, a rigid ring, or other retaining structure. With a rigid ring, the material of cover 260 under the rigid ring can provide the elasticity needed for assembly of the instrument. Some suitable materials for clip 262 include stainless steel, plastic and nitinol.

Figure 2B:
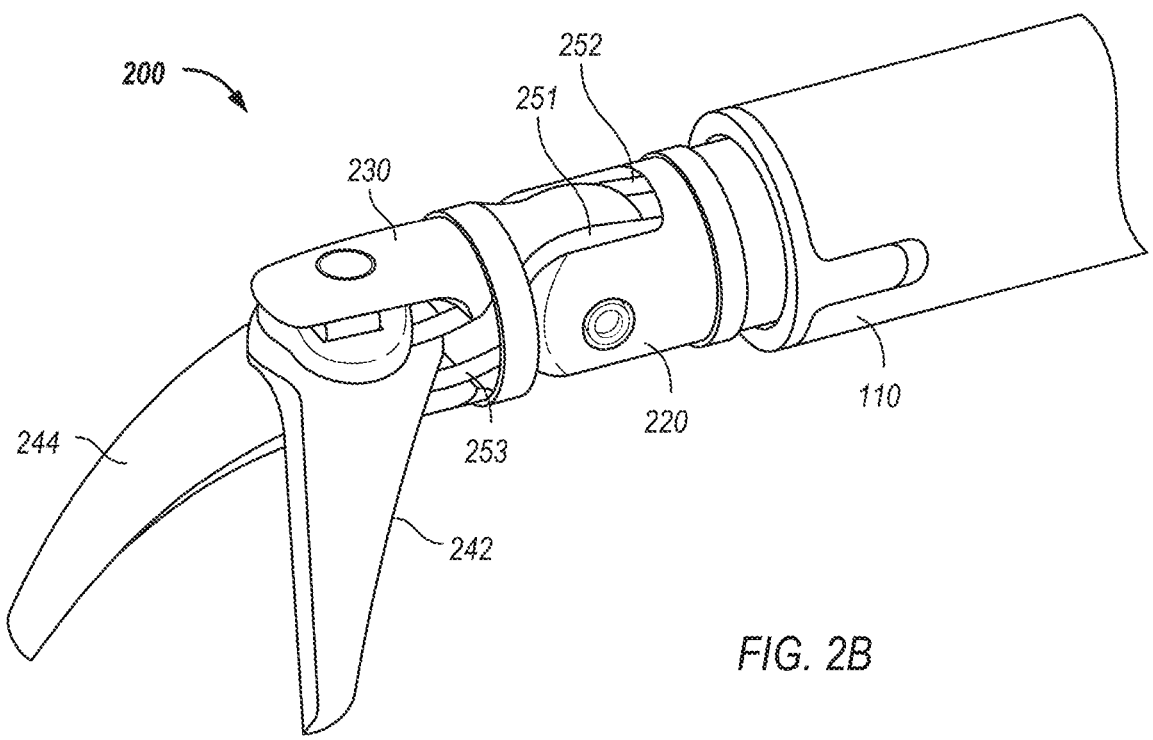

FIG. 2A shows the blades of scissors 240 in the closed position, but a wrist mechanism hidden by cover 260 can open scissors 240 and change the position and orientation of scissors 240 during a medical procedure. FIG. 2B shows end effector 200 with scissors 240 in an open configuration and with cover 260 removed. Scissors 240 include blades 242 and 244 that are pivotally mounted on a distal clevis 230.

Blades 242 and 244 are conductive and can be stamped metal blades. Distal clevis 230 is pivotally mounted on a proximal clevis 220, which is attached to the distal end of main tube 110.

Drive cables are connected to end effector 200 and are used to rotate blades 242 and 244 to change the yaw and grip of end effector 200 and to rotate distal clevis 230 to change the pitch of end effector 200. In one configuration, end effector 200 has only four drive cables that the backend mechanism uses to control the pitch, yaw, and grip motions. Low friction interfaces can be used throughout the instrument to minimize force transmission losses that might otherwise lead to increased cable stretch. In particular, low friction interfaces can be created between the drive cables and the guiding surfaces of proximal and distal devises 220 and 230. Alternatively, pulleys can be provided at the highest friction locations such as where the drive cables apply torque for rotation of distal clevis 230 about a pin in proximal clevis 220. The drive cables can also be swaged to provide smooth, low friction motion. Embodiments of the invention can also be implemented in systems employing more than four drive cables.

Figure 3A:
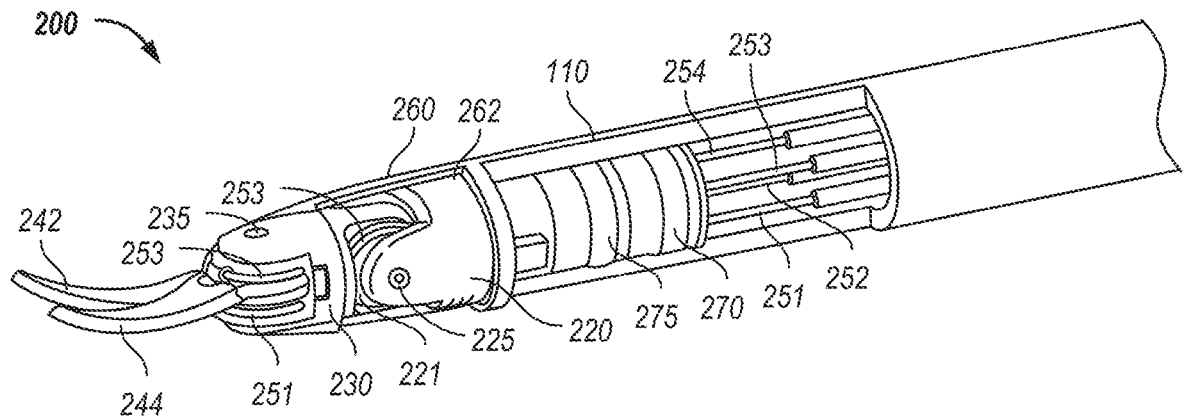
FIGS. 3A and 3C show partial cutaway views of the end effector of FIGS. 2A and 2B.
Figure 3B:
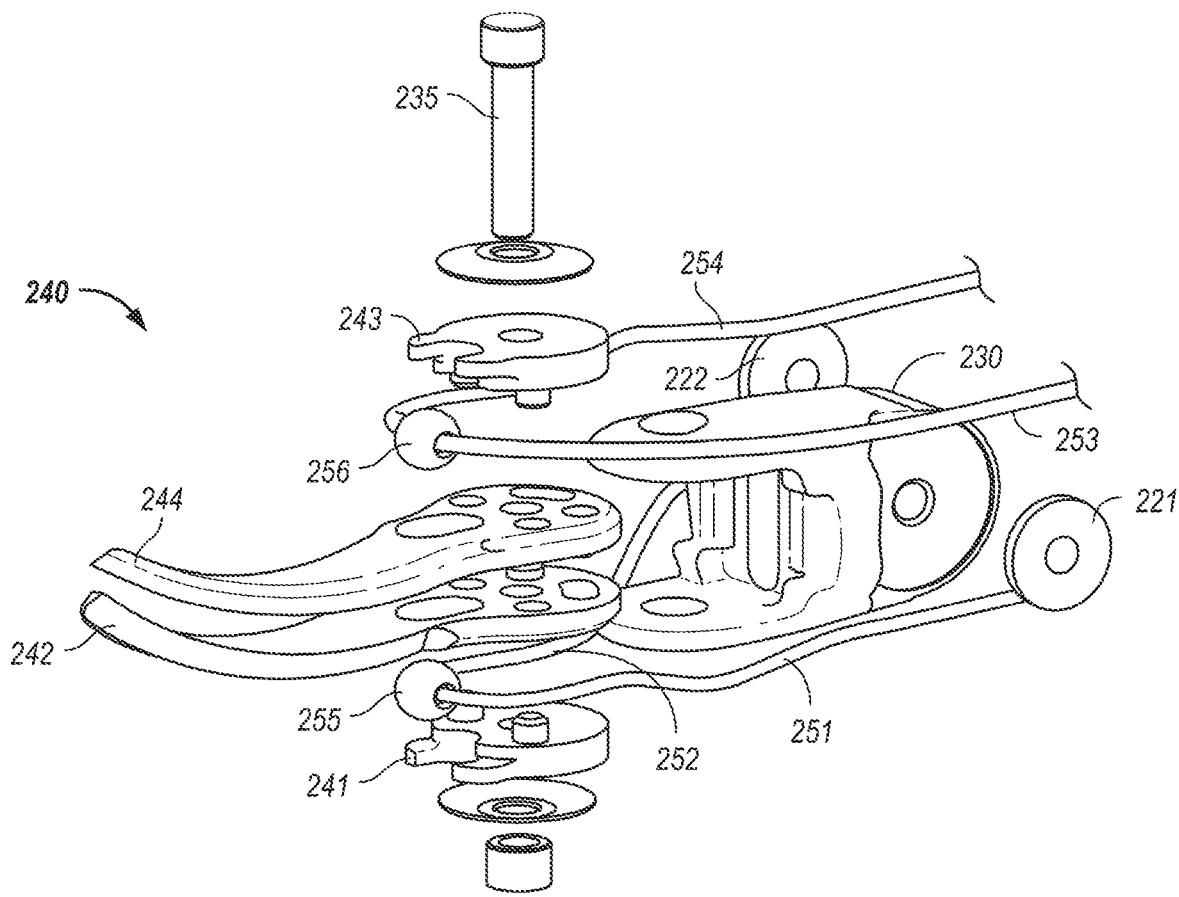
FIG. 3B shows an exploded view of scissors in accordance with an embodiment of the invention.

FIGS. 3A and 3B respectively show a partial cut away view of end effector 200 and an exploded view of scissors 240 to better illustrate the operation of an embodiment of the invention using a four-cable wrist mechanism. End effector 200 includes proximal clevis 220, distal clevis 230, and scissors 240 as described above. Drive cables 251, 252, 253, and 254 are attached to scissors 240. More specifically, each blade 242 or 244 as shown in FIG. 3B has a cap 241 or 243 that locks into blade 242 or 244. Caps 241 and 243 slip onto pin 235 and have a notch that traps a crimp 255 or 256. Alternatively, each cap 241 or 243 can be permanently attached to the corresponding blade 242 or 244 (e.g., by swaging). Caps 241 and 243 can be metal, plastic, or other material that provides the desired strength and cost. Crimp 255 is attached to a cable loop having ends that extend back as cables 251 and 252, and crimp 256 is attached to a cable loop having ends that extend back as cables 253 and 254. When assembled into distal clevis 220, caps 241 and 243 hold crimps 255 and 256 in respective notches, so that cables 251 and 252 are attached to blade 242 and cables 253 and 254 are attached to blade 244.

Cables 251, 252, 253, and 254 are made of a conductive material such as stranded metal cable or metal hypotubes, and may be an assembly with portions made of different materials. For example, portions of cables 251, 252, 253, and 254 in the wrist mechanism can be made of stranded metal cable for flexibility and may be swaged to provide smoother cable surfaces and reduce friction. Portions of cables 251, 252, 253, and 254 extending through main tube 110 may be hypotubes. An electrically insulating coating is not required on any of cables 251, 252, 253, or 254 although one or more of cables 251, 252, 253, or 254 can be used to conduct an electrical signal from the backend mechanism to end effector 240.

Cables 251, 252, 253, and 254 ride on pulleys 221 and 222, and from there extend back through main tube 110 to a backend mechanism (e.g., backend mechanism 120 of FIG. 1). In the illustrated embodiment cables 251 and 253 ride on pulley 221, and cables 252 and 254 ride on pulley 222. A pin 225 in proximal clevis 220 provides an axel for pulleys 221 and 222. Pin 225 also attaches distal clevis 230 to proximal clevis 220 but allows distal clevis 230 to rotate about a pivot axis sometimes referred to herein as the pitch axis. Pulleys 221 and 222 define a radius about pin 225 at which cables 251 and 252 act when rotating distal clevis 230 about pin 225, i.e., about the pitch axis.

When changing the pitch angle of end effector 200, the backend mechanism applies a higher tension to one pair of cables 253 and 254 or 251 and 252, and pulleys 221 and 222 and the distal clevis 230 rotate in a direction depending on which pair of cables 253 and 254 or 251 and 252 has higher tension. The low tension pair of cables 251 and 252 or 253 and 254 pay out at the same rate that the high tension cables are pulled in and therefore also rotate with pulleys 221 and 222. There is no relative sliding or slipping of cables 251, 252, 253, and 254 on pulleys 221 and 222 when the pitch of end effector 200 is changed. Rotation of pulleys 221 and 222 about pivot pin 225 results in lower cable friction than if cable 251, 252, 253, and 254 were sliding over an integral sliding surface in distal clevis 230.

A pin 235 in distal clevis 230 is perpendicular to pin 225 and defines a pivot axis, sometimes referred to as the yaw axis or grip axis, for scissors 240 as a whole or blades 242 and 244 individually. The yaw axis and the grip axis coincide in end effector 200. The term grip is used herein in a general sense since the action of blades 242 and 244 is generally to cut as blades 242 and 244 close or grip.

Opening or closing the grip of blades 242 and 244 without changing the yaw angle of end effector 200 requires high tension on cables that are on opposite sides of distal clevis 230. For example, to close jaws 242 and 244, high tension is applied to cables 251 and 254. Equal lengths of cables 251 and 254 are pulled in as the same length of cables 252 and 253 are payed out. As a result, relative to the view of FIG. 3B, pulley 221 rotates counterclockwise, pulley 222 rotates clockwise, and cables 251, 252, 253, and 254 do not slide or slip on pulley 221 or 222 when closing jaws 242 and 244. Opening blades 242 and 244 switches the tension in cables 251, 252, 253, and 254 and reverses the directions of rotation of pulleys 221 and 222 but still avoids sliding on pulleys 221 and 222.

Some of cables 251, 252, 253, and 254 can slide or slip in the groove of or move relative to the rotation of pulleys 221 or 222 when the yaw angle of blades 242 and 244 is being changed. For example, the yaw of end effector 200 can be changed by pulling in (or paying out) equal lengths of cables 251 and 253 while paying out (or pulling in) the same lengths of cables 252 and 254. When the pitch angle of end effector 200 is zero as shown in FIGS. 3A and 3B, at least one of cables 251 and 253 will slide on pulley 221, and at least one of cables 252 and 254 will slide on pully 222. The sliding friction that resists a cable's movement will then depend on the wrap angle of the cable on its associated pulley 221 or 222 and the component cable tension pulling the cable on to its pulley 221 or 222. With a pitch angle of zero, the wrap angles of cables on pulleys 221 and 222 are relatively small and the sliding friction is relatively small.

Figure 3C:
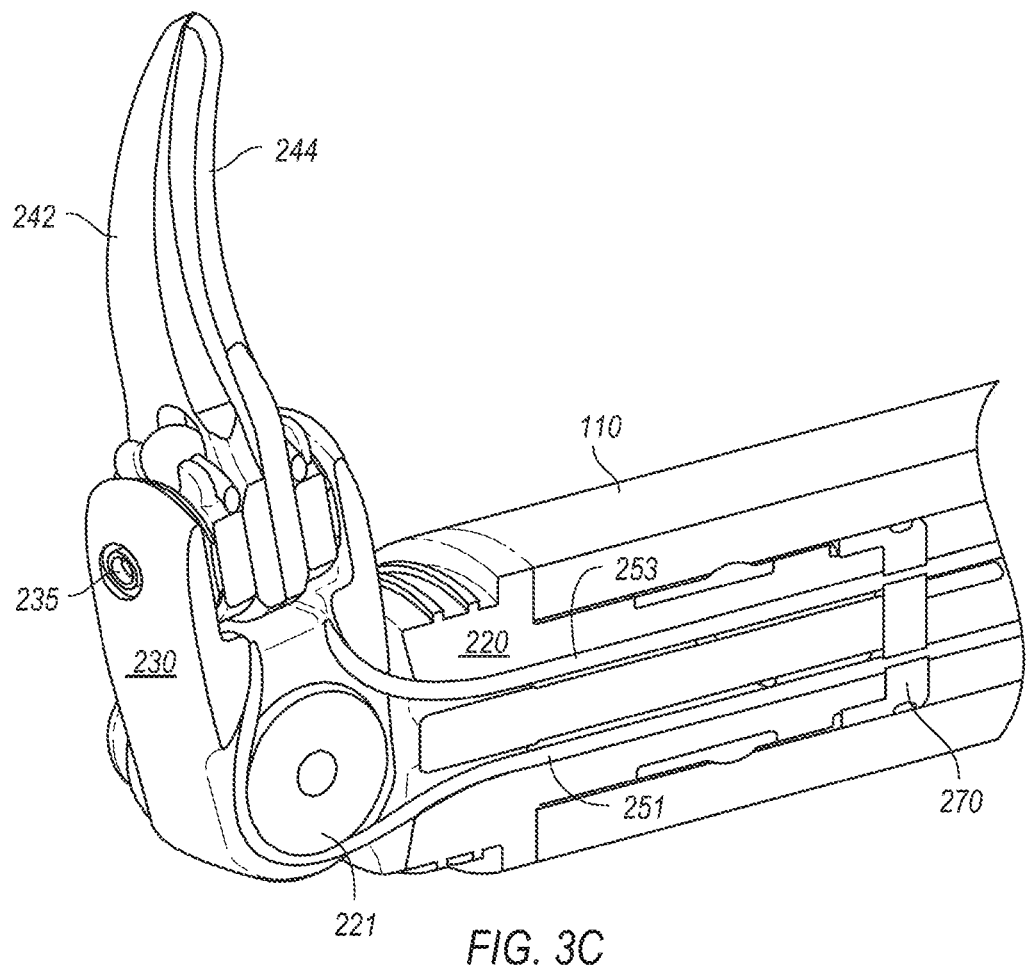

A non-zero pitch angle of end effector 200 will cause cable 251 to have a wrap angle around pulley 221 that differs from the wrap angle of cable 253 around pulley 221 and cause cable 252 to have a wrap angle around pulley 222 that differs from the wrap angle of cable 254 around pulley 222. FIG. 3C illustrates how a large pitch angle of distal clevis 230 causes cable 251 to have a large wrap angle on pulley 221 and lifts cable 253 off of pulley 221. When high tension is applied to cables 251 and 253 to causes blades 242 and 244 to rotate in the same direction, cable 253 slides on solid surfaces of devises 220 and 230, but pulley 221 rotates as cable 251 moves, resulting in lower friction for cable 251 than if cable 251 were sliding over an integral sliding surface in distal clevis 230.

Both cables 251 and 253 may contact pulley 221 but have different wrap angles when distal clevis 230 has other pitch angles. In these configurations, the cable 251 or 253 exerting greater force on pulley 221 will rotate with pulley 221 during rotation of blades 242 and 244 to change the yaw angle of end effector 200. The other cable 253 or 251 then slides on pulley 221, but that cable has smaller force/wrap angle on pulley 221. Similarly, cables 252 and 254 will generally have different wrap angles on pulley 222, and the cable that exerts the greater force on pulley 222 (and that would therefore experience greater sliding friction) moves with the rotation of pulley 222.

The use of a single pulley for a pair of cables as in end effector 200 thus usually reduces cable friction when compared to cables riding solely on solid fixed surfaces. Use of one pulley for two cables also conserves space and reduces part count when compared to a traditional pulley system including a pulley for each cable (or four pulleys total for a four cable system). However, alternative embodiments of the invention can employ other pulleys structures to reduce cable friction. Alternatively, to provide lower component count and costs, pulleys 221 and 222 can be eliminated and guide channels such as described in the co-filed patent application entitled, "Four-Cable Wrist with Solid Surface Cable Channels," which was incorporated by reference above, could be used to guide the drive cables and define the moment arm for torques causing pitch rotations.

Figure 4A:
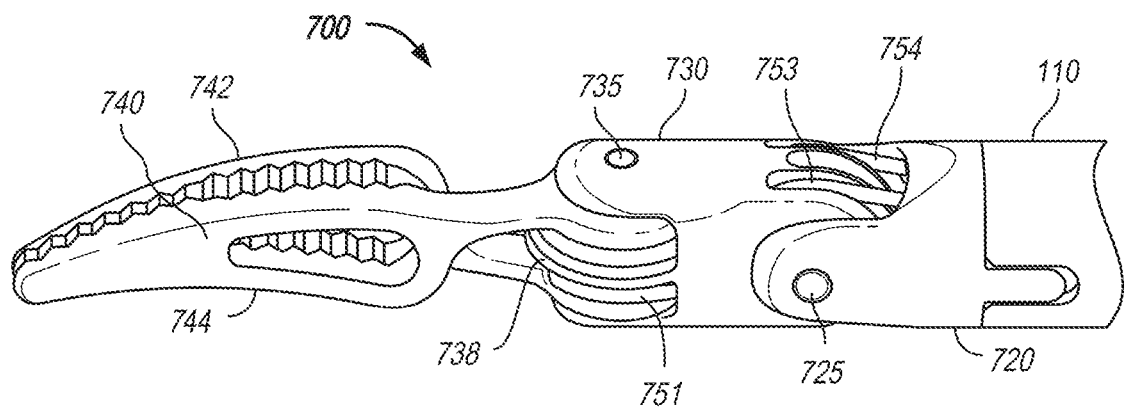
FIGS. 4A, 4B, and 4C show a wrist mechanism in accordance with an embodiment of the invention using a pair of devises and four drive cables that slide on guide surfaces integrated into the devises.
Figure 4B:
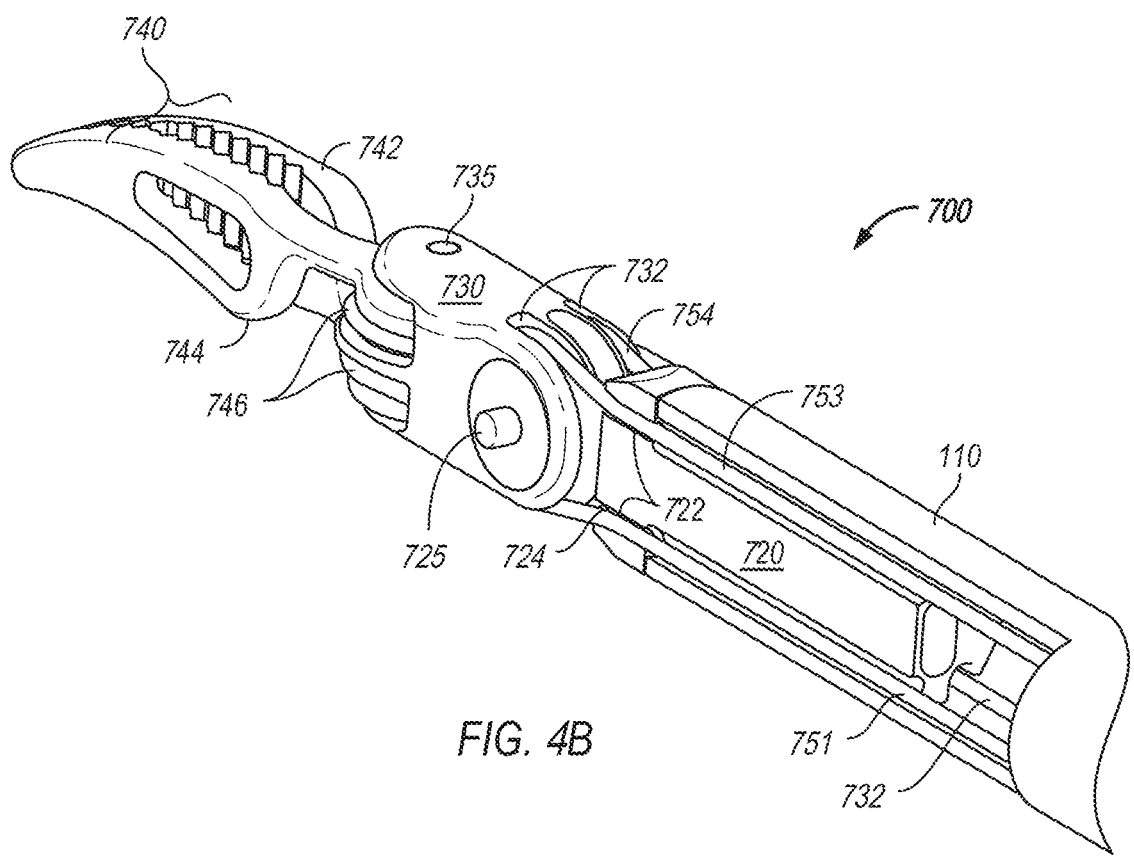
Figure 4C:
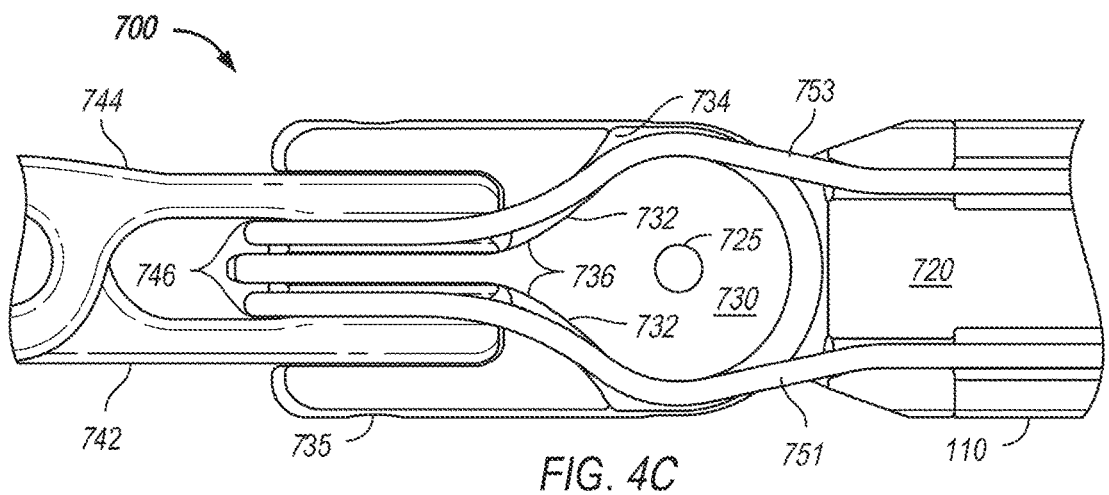

For example, FIGS. 4A, 4B, and 4C show three views of a wrist mechanism 700 in accordance with an embodiment of the invention. As illustrated in FIG. 4A, wrist mechanism 700 includes a proximal clevis 720, a distal clevis 730, and an effector 740. Effector 740 includes jaws 742 and 744, each having a grip portion attached to a circular hub. Cables 751, 752, 753, and 754 are attached to effector 740, extend along solid surfaces of guide channels in effector 740, distal clevis 730, and proximal clevis 720, and from there extend back through main tube 110 to a backend mechanism (e.g., backend mechanism 120 of FIG. 1). The low part count of wrist mechanism 700 and the small number of drive cables 751, 752, 753, and 754 employed facilitate implementation of a small diameter for wrist mechanism 700 and main tube 110. Additionally, the low part count allows cost effective use of wrist mechanism in a single-use instrument, i.e., an instrument that is disposed of after a single medical procedure, instead of being an instrument that must be sterilized for subsequent use.

The partial cutaway view of wrist mechanism 700 in FIG. 4B shows how proximal clevis 720 can extend into and attach to main tube 110. A pin 725 in proximal clevis 720 attaches distal clevis 730 to proximal clevis 720 but allows distal clevis 730 to rotate about a pivot axis (sometimes referred to herein as the pitch axis) defined by pin 725. Proximal clevis 720 includes guide channels 722 for cables 751, 752, 753, and 754, and openings 724 of the guide channels 722 provide a range of motion for cables 751, 752, 753, and 754 that directs cables 751, 752, 753, and 754 into guide channels 732 of proximal clevis 730. In an exemplary embodiment, openings 724 of guide channels 722 are narrow in the direction parallel to pin 725 in order to direct cables 751, 752, 753, and 754 into respective guide channels 732 in distal clevis 730 but fan out in a direction perpendicular to pin 725 to keep cable friction low over the range of pitch angles that wrist mechanism 700 provides for distal clevis 730. Similarly, openings 734 of guide channels 732 nearest proximal clevis 720 are narrow in a direction parallel to the pitch axis and pin 725 but fan out in a direction perpendicular to pin 725 to accommodate pitch rotations and avoid pinching cables 751, 752, 753, and 754.

Guide channels 732 in distal clevis 730 define a radius about pin 725 at which cables 751, 752, 753, and 754 act on distal clevis 730 when rotating distal clevis 730 about pin 725, i.e., about the pitch axis. In order for the moment arm of the torque applied by the cables to be constant throughout the range of pitch motion of wrist mechanism 700, guide channels 732 have surfaces approximately in the shape of circular arcs. When distal clevis 730 is in the position illustrated in FIG. 4C, cable 753 has a portion that rests against a lower guide surface subtending a circular arc about the pitch axis of pin 725, and the distance between the pitch axis and the contact point of cable 753 on the lower surface of guide channel 732 is the moment arm for torque applied through cable 753. In the view of FIG. 4C, distal clevis 730 rotates clockwise when the backend mechanism pulls in cable 753. If clockwise rotation continues from the illustrated position, cable 753 will remain on the surface and act at a constant moment arm until distal clevis 730 reaches the limit of its range of motion. Further, through the entire motions, the surfaces of guide channels 732 that are circular arcs pull in and play out equal lengths of cable as distal clevis 730 rotate, thereby avoiding cable slack.

The cross-section of distal clevis 730 in FIG. 4C further illustrates how guide channels 732 extend through distal clevis 730 and direct cables 751, 752, 753, and 754 into circular guide channels 746 that are integrated into jaws 742 and 744 of effector 740. In particular, four guide channels 732 tunnel through distal clevis 730 for the four cables 751, 752, 753, and 754. Openings 736 of guide channels 732 nearest effector 740 direct cables 751, 752, 753, and 754 into respective guide channels 746 in jaws 742 and 744.

A pin 735 in distal clevis 730 is perpendicular to pin 725 and defines a pivot axis, sometimes referred to as the yaw axis or grip axis, for effector 740 as a whole or jaws 742 and 744 individually. (The yaw axis and the grip axis coincide in wrist mechanism 700.) Guide channels 746 of jaws 742 and 744 are circular and centered on pin 735, so that the radius of channels 746 is the moment arm for torques that cables 751, 752, 753, and 754 apply to jaws 742 and 744 when rotating jaws 742 and 744 or when maintaining a gripping force of jaws 742 and 744. The term gripping is used herein in a general sense since the action of jaws 742 and 744 depend on the work tips of jaws 742 and 744. In the illustrated embodiment of FIGS. 4A, 4B, and 4C, the working tips of jaws 742 and 744 have a surface for gripping and may be used, for example, in forceps or cautery applications. Alternatively, "gripping," which closes jaws 742 and 742, may be a cutting action when the tips of jaws 743 and 744 are blades that cooperatively cut as a scissors. Gripping can thus perform different functions depending on the nature of effector 740.

The paths of cables 751, 752, 753, and 754 through wrist mechanism 700 do not employ pulleys. Instead of pulleys, wrist mechanism 700 guides cables 751, 752, 753, and 754 as described above using solid surfaces (i.e., the surfaces of guide channels 722 and 732) that are integral to devises 720 and 730. At some points, the guiding surfaces cradle opposing sides of the cable. For example, top and bottom surfaces of cable 753 as shown in FIG. 4C contact guide surface 732 at an inflection point 737 where the curvature of cable 753 changes. The solid guide surfaces are also curved to eliminate the need for large cable wrap angles and to maintain a fixed cable radius or moment arm. Large wrap angles were necessary in some prior wrist mechanisms to maintain a constant cable radius about the pivot axis throughout the range of motion. The surfaces of guide channels 722 and 732 can additionally be shaped to retain (or avoid derailment of) cables 751, 752, 753, and 754 and to keep cables 751, 752, 753, and 754 within the diameter constraint of a cannula through which wrist mechanism 700 passes during a minimally invasive medical procedure.

Guiding cables 751, 752, 753, and 754 experience less friction when compared to wrist mechanisms with larger cable wrap angles. Friction of cables 751, 752, 753, and 754 against distal clevis 730 and elsewhere may also be reduced through selection of the materials used. In particular, distal clevis 730 can be made of a plastic that provides low friction against the material of cables 751, 752, 753, and 754. Additionally, in some embodiments, cables 751, 752, 753, and 754 include portions of stranded metal cable that may be swaged to provide smoother cable surfaces that lower friction. The reduced cable friction allows pulleys to be deleted while maintaining clinically acceptable forces, torques, and precision and fidelity of motion for wrist mechanism 700. Avoiding the use of pulleys reduces the space requirements of wrist mechanism 700, allowing wrist mechanism 700 to have a clinically beneficial smaller working volume. Eliminating pulleys also reduces the cost.

Cables 751 and 752 attach to jaw 742 of effector 740, and cables 753 and 754 attach to jaw 744 of effector 740. The attachment of cables 751 and 752 to jaw 742 is such that pulling in a length of one cable 751 or 752 while releasing the same length of the other cable 752 or 751 causes jaw 742 to rotate about pin 735. Similarly, the attachment of cables 753 and 754 to jaw 744 is such that pulling in a length of one cable 753 or 754 while releasing the same length of the other cable 754 or 753 causes jaw 744 to rotate about pin 735. Many techniques for attaching cables 751, 752, 753, and 754 could be employed. For example, in a typical attachment, cables 751 and 752 (or cables 753 and 754) are opposite end portions of a cable loop that extends around circular arc about pin 735 that guide channel 746 defines in jaw 742 (or 744), and an attachment can be created by a knot tied in or a crimp fastened on the loop and fit into a matching notch (not shown) in guide channel 746. However, reliably attaching a crimp to some cable materials, e.g., non-conductive cable materials can present challenges. To avoid crimping, the cable loop may terminate through a high-friction pathway in jaw 742 or 744, so that friction prevents cables 751, 752, 753, and 754 from slipping relative to jaws 742 or 744.

Figure 5A:
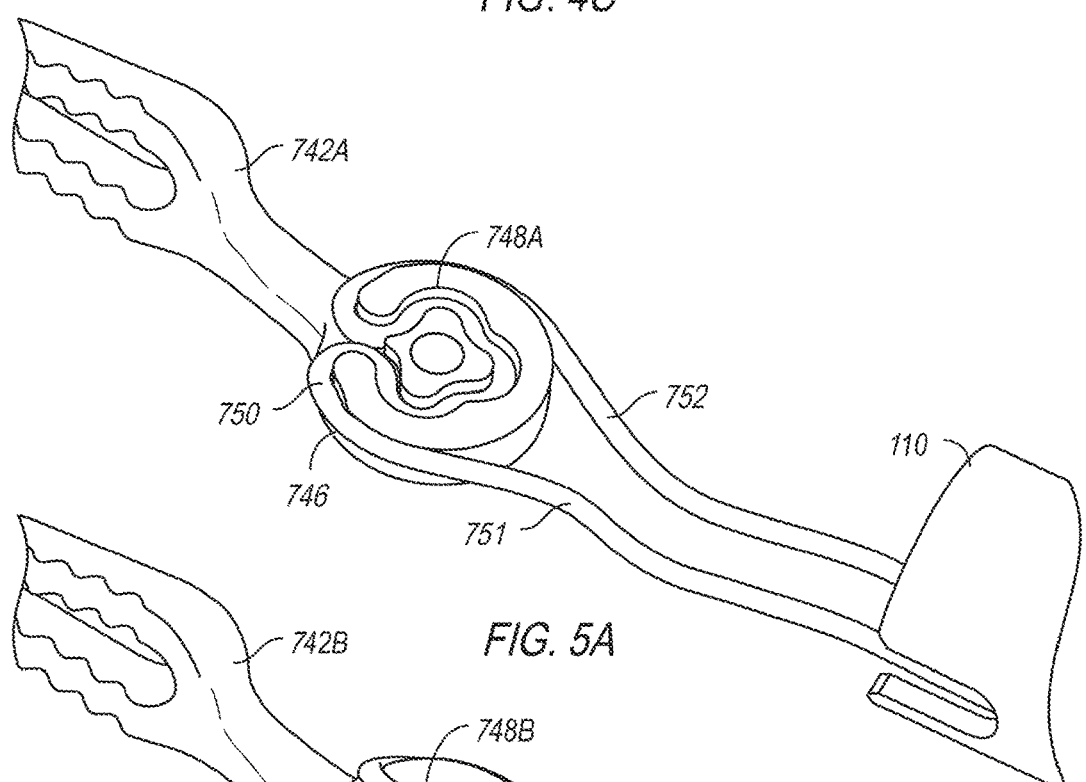
FIGS. 5A and 5B illustrate jaws with cables attached using high friction paths in accordance with alternative embodiments of the invention.

FIG. 5A shows a jaw 742A attached to a cable loop 750 having portions that extend back into main tube 110 as to cables 751 and 752. Loop 750 extends along circular arcs of guide channel 746 of jaw 742A into a high friction path 748A, and back out along another circular arc of guide channel 746. Path 748A is substantially co-planar with guide channel 746 and includes multiple sharp bends. Contact between cable loop 750 and the surface of jaw 742A at the bends in path 748A creates friction that prevents or resists sliding of cable 750, each bend increasing the frictional force that acts to retain cable loop 750 against pullout. Cable loop 750 has no crimp attached.

Figure 5B:
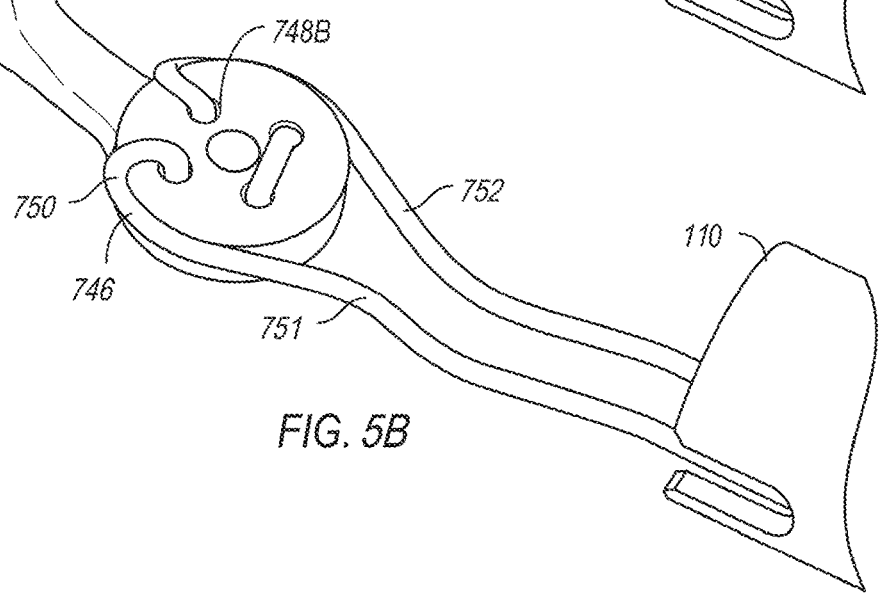

FIG. 5B shows a jaw 742B using an alternative high friction path 748B in which cable loop 750 is threaded through several holes in jaw 742B. Contact of cable loop 750 with jaw 742B at the bends in cable loop 748B (including at locations where cable loop 750 passes through jaw 742B) creates friction that resists or prevents sliding of cable loop 750. Accordingly, a crimp is not required to attach cable loop 750 to jaw 742B. Assembly of a wrist mechanism using high friction path 748B requires threading of cable through holes in jaw 742B, but once threaded, cable loop 750 is solidly retained in jaw 742B, which may make assembly of a wrist using high friction path 748B of FIG. 5B simpler than assembly of a wrist using high friction path 748A of FIG. 5A.

The jaw attachments without crimps eliminate the space requirement of crimps and the cost associated with crimping. The attachments without crimps are also advantageous for some cable materials (e.g. non-metallic cables) for which crimping can be troublesome. As described further below, non-metallic cables can be useful as electrical insulators in cauterizing instruments. Even instruments that do not require electrical insulation, non-metallic cables may provide reduced friction, wear, and particulate generation against mating surfaces in the wrist mechanism.

Figure 6A:
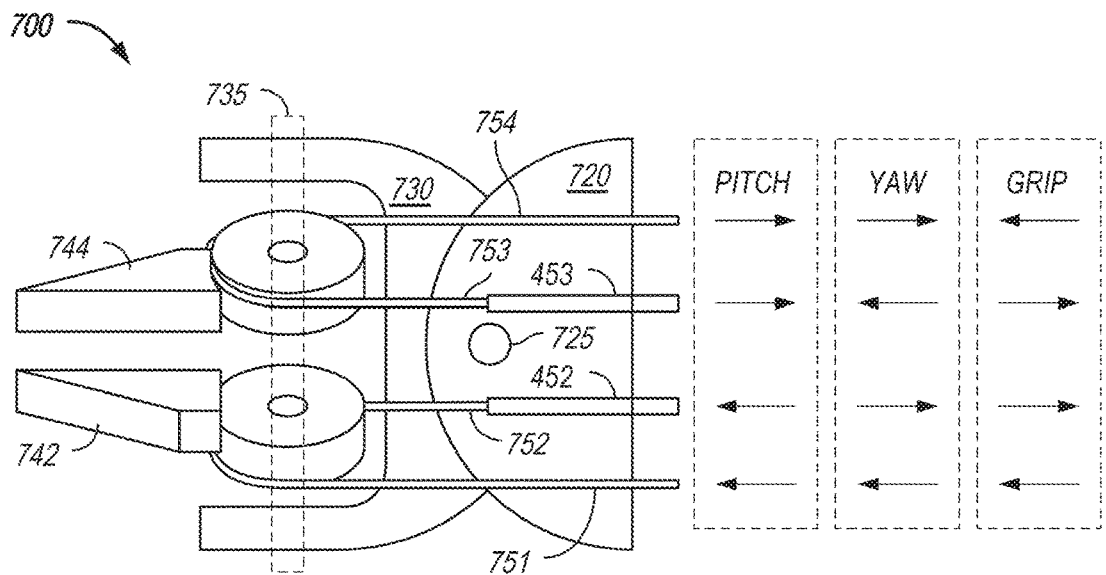
FIG. 6A illustrates the movements of four drive cables that produce changes in the pitch, yaw, and grip of a wrist mechanism in accordance with an embodiment of the present invention.
Figure 6B:
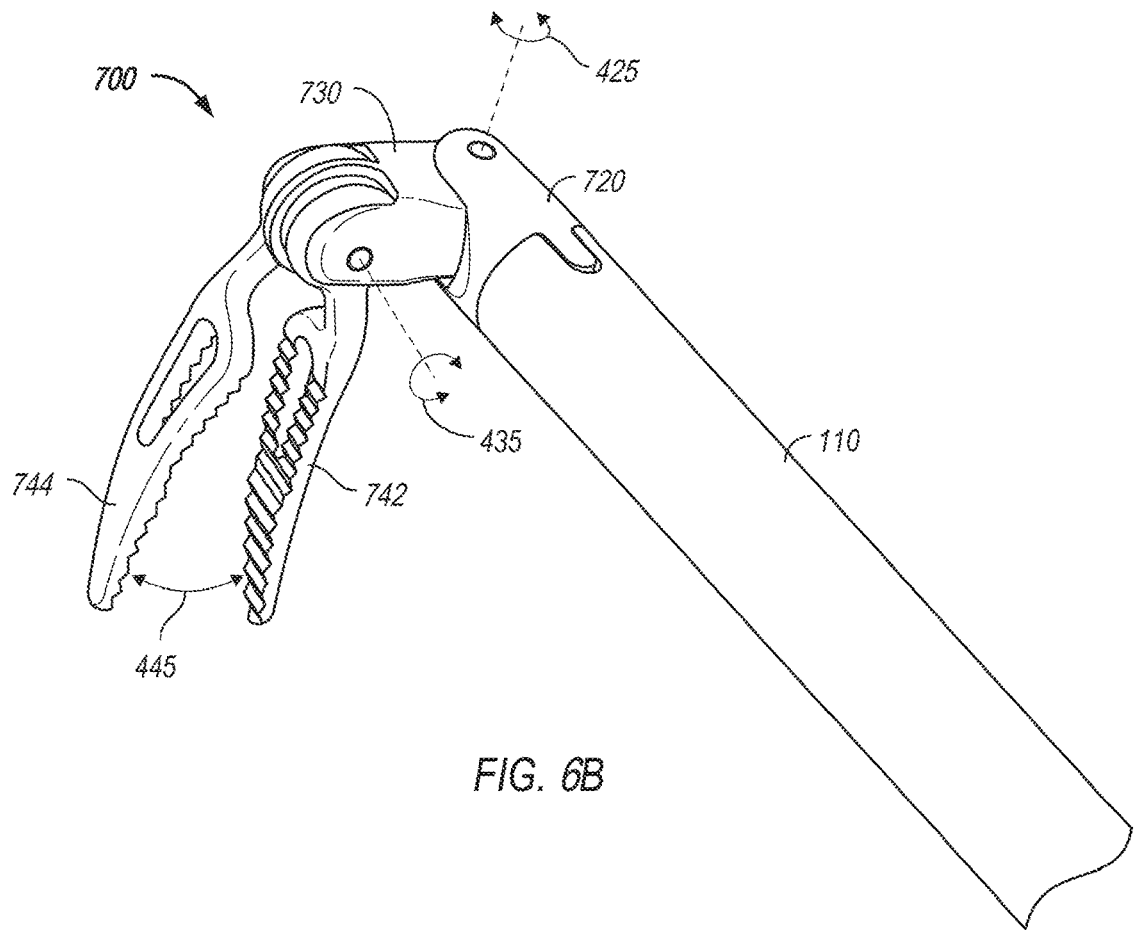
FIG. 6B shows a perspective view illustrating pivot axes of the wrist mechanism of FIGS. 4A, 4B, and 4C when operated using the cable movements of FIG. 6A.

Changing the pitch, yaw, or grip of the wrist mechanism 700 described above generally requires movements or actions respectively applied to four cables 751, 752, 753, and 754. FIG. 6A shows a simplified view of wrist mechanism 700 and illustrates processes for changing the pitch, yaw, and grip of jaws 742 and 744. The illustrated processes can generally be performed one at a time or simultaneously in any desired combination to change the pitch, yaw, and grip of mechanism 700. FIG. 6B shows wrist mechanism 700 in more detail to illustrate rotation axes of wrist mechanism 700 and is described here simultaneously with FIG. 6A.

Pitch axis rotations, i.e., rotations 425 in FIG. 6B, rotate distal clevis 730 about the pitch axis defined by pin 725. For clockwise rotation about the pitch axis, a backend mechanism (not shown) pulls in identical lengths of cables 753 and 754 while releasing the same lengths of cables 751 and 752. Cables 753 and 754 apply forces to distal clevis 730 at moment arms defined by the guide channels of cables 753 and 754 through distal clevis 730. Similarly, for counterclockwise rotation of clevis 730 about the pitch axis, the backend mechanism pulls in identical lengths of cables 751 and 752 while releasing the same lengths of cables 753 and 754.

Yaw rotations, i.e., rotations 435 in FIG. 6B, corresponds to both rotating jaws 742 and 744 in the same direction and through the same angle. In particular, the backend mechanism pulling in a length of cable 752 and releasing an equal length of cable 751 will cause jaw 742 to rotate in a clockwise direction about the axis of pin 735. For this rotation, the guide channel in jaw 742 defines the moment arm at which cable 752 applies a force jaw 742, and the resulting torque causes jaw 742 to rotate clockwise and cables 751 and 752 to slide on the solid surface of guide channels in distal clevis 730. If at the same time the backend mechanism pulls in a length of cable 754 and releases the same length of cable 753, jaw 744 will rotate clockwise through an angle that is the same as the angle through which jaw 742 rotates. Accordingly, jaws 742 and 744 maintain their positions relative to each other and rotate as a unit through a yaw angle. Counterclockwise rotation of the effector including jaws 742 and 744 is similarly accomplished when the backend mechanism pulls in equal lengths of cables 751 and 753 while releasing the same lengths of cables 752 and 754.

Grip rotations, i.e., rotations 445 in FIG. 6B, are achieved by rotating jaws 742 and 744 in opposite directions by the same amount. To open the grip of jaws 742 and 744, the backend mechanism pulls in equal lengths of cables 751 and 754 while releasing the same lengths of cables 752 and 753, causing jaws 742 and 744 to rotate in opposite directions away from each other. To close the grip of jaws 742 and 744, the backend mechanism pulls in equal lengths of cables 752 and 753 while releasing the same lengths of cables 751 and 754, causing jaws 742 and 744 to rotate in opposite directions toward each other. When faces of jaws 742 and 744 come into contact, the tension in cables 752 and 753 can be kept greater than the tension in cables 751 and 754 in order to maintain gripping forces.

FIG. 6A illustrates that portions 452 and 453 of cables 752 and 753, respectively, can be made stiffer or thicker than corresponding portions of cables 751 and 754 to accommodate the higher or maintained tensions used for gripping. This can be achieved by fusing the ends of cable loops corresponding to cable 752 or 753 with heavier material. In a typical embodiment of the invention, portions of cables 751, 752, 753, and 754 having larger flexing during cable movement can be made of a flexible material such as a stranded metal cable. Relatively straight portions of each cable (e.g., portions extending back through the main tube) in some embodiments can be less flexible material such as hypotubes or similar structures that have advantages in cost and immunity to stretching, and in such an embodiment, larger hypotubes can be used for portions 452 and 453 of cables 752 and 753. The effective stiffness of each of the four drive cables 751, 752, 753, and 754 can thus be controlled advantageously for improved clinical performance. In particular, the effective stiffness of drive cables 752 and 753 that cause jaws 742 and 744 to close is greater than the stiffness of drive cables 751 and 752 that cause jaws 742 and 744 to open. This arrangement minimizes cable slack, improving the fidelity of motion of wrist mechanism 700. Materials, diameters, and lengths (e.g., of portions 452 and 453) are controlled to affect desired stiffness. Not using the larger structures in cables 751 and 754 saves cost and space.

A backend mechanism can change the pitch, yaw, or grip of scissors 240 or any combination of pitch, yaw, and grip through manipulation of cables 251, 252, 253, and 254 as described above. For example, the backend mechanism pulling in the same length of cables 251 and 252 while releasing an equal length of cables 253 and 254 causes clevis 230 to rotate about pin 225, e.g., to pitch downward in FIG. 3B. Similarly, the backend mechanism pulling in the same length of cables 253 and 254 while releasing an equal length of cables 251 and 252 causes clevis 230 to pitch upward in FIG. 3B. Pulling in a length of one cable 251 or 252 while releasing an equal length of the other cable 252 or 251 causes blade 242 to rotate about pin 235. Similarly, pulling in a length of one cable 253 or 254 while releasing an equal length of the other cable 254 or 253 causes blade 244 to rotate about pin 235. The backend mechanism can thus change the yaw of scissors 240 by rotating both blades 242 and 244 in the same direction through the same angle. The grip of scissors 240 can be changed by rotating both blades 242 and 244 in opposite directions through the same angle.

Scissors 240 are designed such that the constraining surfaces that maintain blade cutting forces are all metal. In particular, pin 235 has an expanded head portion and an opposite end cap that constrain blades 242 and 244 from separating during cutting. This ensures consistent closing force of blades 242 and 244 throughout their life while making for a low friction interface when pivoting in distal clevis 230. Further, distal clevis 230 can be made of plastic or other insulating material and does not require the strength/rigidity to prevent blades 242 and 244 from being pushed apart during cutting.

The use of metal cables 251, 252, 253, and 254 attached to metal blades 242 and 244 for actuation also permits use of cables 251, 252, 253, and 254 to electrically energize blades 242 and 244. This avoids the need for additional conductors in main tube 110 and for additional electrical connectors in end effector 200. In an embodiment used for monopolar scissors, all metal parts in end effector 200 are electrically energized with the same signal at the same time, e.g., whenever a cauterizing function of scissors 240 is activated. As mentioned above, main tube 110 can be made of insulating material and a cover 260, which is held on main tube 100 using compression ring 262, can encapsulate cables 251, 252, 253, and 254 and most of the components of end effector 200, leaving blades 242 and 244 as the only electrically energized components that are exposed and able to contact the patient. Additionally, insulating plastic components can be used throughout the instrument where strength requirements permit, for example, proximal clevis 220 and distal clevis 230 can be made of plastic or other insulating material. Plastic components may also reduce friction where cables ride on solid surfaces.

Seals may be employed at the end of main tube 200 to isolate electrically energized cables from conductive fluids that may be in contact with the instrument during a medical procedure. The partial cutaway view of end effector 200 in FIG. 3A shows how proximal clevis 220 can extend into main tube 110 and how multiple seals 270 and 275 can be used to prevent fluid flow. Limiting contact to conductive fluids is desired because liquid in contact with energized cables can directly conduct the full working voltage from the cables to the patient and cause alternate site burns. The seals create a barrier to break that the direct conductive path. Additionally, the signal conducted through main tube 110 has a capacitive coupling to the surrounding environment outside main tube 110. This capacitive coupling can cause currents in surrounding liquids, and those currents waste power, lower the working voltage on blades 242 and 244, and could cause alternate site burns. The strength of the capacitive coupling and the magnitude of the capacitive leakage currents depend on factors such as the diameter and length of conductor (e.g., cable 251, 252, 253, or 254), the insulating properties of main tube 110, and the separation between the conductor within main tube 110 and the external environment. If main tube 110 were to fill with conductive fluid, the effective distance between the conductor portion inside main tube 110 and the external environment would be smaller and capacitive coupled current leaked to the patient would be greater.

Figure 7:
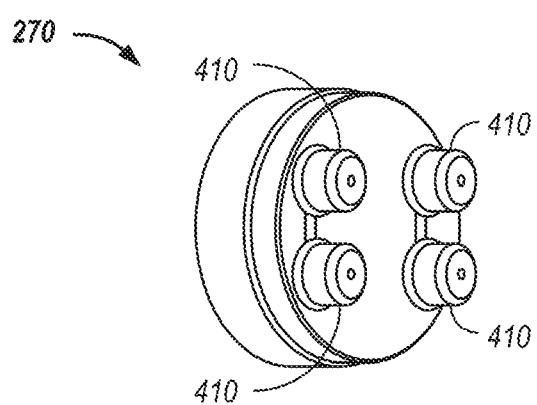
FIG. 7 shows an embodiment of a seal suitable for use in a medical instrument in accordance with an embodiment of the invention.

An embodiment of end seal 270 is illustrated in FIG. 7. Seal 270 as shown has a diameter that fits tightly inside main tube 110 and four projections 410 through which cables 251, 252, 253, and 254 extend. Seal 270 can be made of silicon or a similar flexible material capable of sealing against main tube 110 and cables 251, 252, 253, and 254 and flexing when cables 251, 252, 253, and 254 move for actuation of scissors 240.

A variety of multi-seal systems could be employed to isolate a patient or user of the instrument from electrical burn hazards. FIG. 3A shows one example where end effector 200 employs cover 260 and seals 270 and 275 in main tube 110 for these purposes. More generally, seals can be used around the cables and between the proximal clevis and the main tube to limit fluid flow into main tube, which could flow out the back end of the instrument. A rib seal can be used between the proximal clevis and the tip cover to obstruct fluid flow from the inside to the outside of the tip cover, which is important because fluid from the inside of the tip cover would be at full cautery voltage and could cause alternate site burns in a patient. Redundant seals can also be used to improve reliability.

Figure 8A:
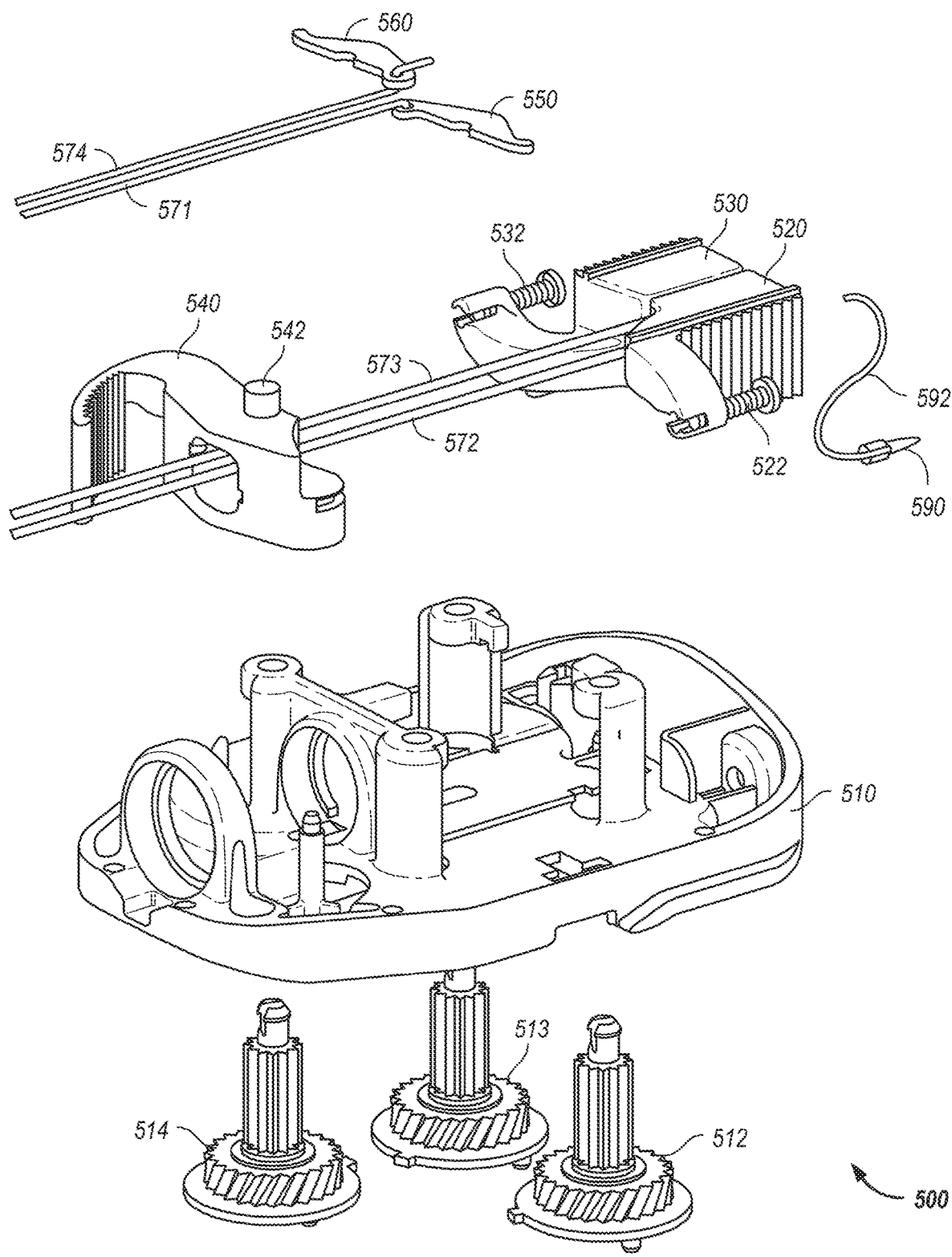
FIGS. 8A and 8B, respectively, show an exploded view and a cross-sectional view of a backend mechanism in accordance with an embodiment of the invention using gears and levers to move drive cables and an electrical connection to energize at least one of the drive cables.

Electrical connection to at least one of cables 251, 252, 253, or 254 can be made in the backend mechanism that manipulates cables 251, 252, 253, or 254. FIG. 8A shows an exploded view of a portion of a backend mechanism 500 in accordance with an embodiment of the invention predominantly employing gears and levers to control movement of a wrist mechanism or end effector. The illustrated portion of backend mechanism 500 couples to four drive cables 571, 572, 573, and 574 and includes a chassis 510, three drive shafts 512, 513, and 514, three toothed components 520, 530, and 540, and two levers 550 and 560. The components 510, 520, 530, 540, and 550 and 560 can be made of any suitably durable material such as molded or machined plastic or metal depending on the required loads and tolerances of the individual components. However, components such as chassis 510 and drive gears 512, 513, and 514 which are externally accessible are preferably made of plastic or another insulating material. As described further below, cables 571, 572, 573, and 574 can correspond to cables 251, 252, 253, and 254 and connect to an end effector of the type described above with reference to FIGS. 2A, 2B, 3A, and 3B. However, backend mechanism 500 can more generally be used in any instrument that can be electrically energized by drive cables and uses connections of four drive cables to three motor driven axes.

Chassis 510 may have a footprint chosen for connection to a robotic control system containing motors that operate drive shafts 512, 513, and 514. In particular, chassis 510 may be shaped such that drive shafts 512, 513, and 514 when fit into chassis 510 are positioned to be engaged and rotated by a robotic control such as the da Vinci system available from Intuitive Surgical, Inc.

Drive shaft 512 acts as a pinion that engages a rack portion of toothed component 520. Toothed component 520 is attached to cable 572 and moves in a straight line to pull in or release a length of cable 572 as gear 512 turns. Toothed component 520 also includes an arm containing an adjustment screw 522 that contacts lever 550. In particular, adjustment screw 522 contacts lever 550 at an end opposite to where cable 571 attaches to lever 550. A pivot point or fulcrum for lever 550 is on toothed component 540, which acts as a rocker arm as described further below. In operation, as toothed component 520 moves, adjustment screw 522 causes or permits rotation of lever 550 about the pivot point so that lever 550 can pull in or release cable 571. The connection of cable 571 to lever 550 and the contact point of adjustment screw 522 on lever 550 can be made equidistant from the pivot point of lever 550, so that when toothed component 520 pulls in (or releases) a length of cable 572, lever 550 releases (or pulls in) the same length of cable 571. Adjustment screw 522 permits adjustment of the tension in cable assembly 571 and 572 by controlling the orientation of lever 550 relative to the position of toothed component 520.

Drive shaft 513 similarly acts as a pinion that engages a rack portion of toothed component 530. Toothed component 530 is attached to drive cable 573 and moves in a straight line to pull in or release a length of cable 573 as gear 513 turns. Toothed component 520 also includes an arm containing an adjustment screw 532 that contacts lever 560 at an end opposite to where cable 574 attaches to lever 560. A pivot point or fulcrum for lever 560 is on rocker arm 540 as described further below, and the distance of the connection of cable 574 from the pivot point of lever 560 can be made the same as the distance from the pivot point of lever 560 to the contact point of adjustment screw 532 on lever 560. As a result, when toothed component 550 pulls in (or releases) a length of cable 573, lever 560 releases (or pulls in) the same length of cable 574. Adjustment screw 532 permits adjustment of the tension in cable assembly 573 and 574 by controlling the orientation of lever 560 relative to the position of toothed component 530.

Drive shafts 512 and 513 can be operated to change the yaw angle or the grip of a wrist mechanism using the processes described above. For example, when cables 571, 572, 573, and 574 respectively correspond to cables 251, 252, 253, and 254 of FIG. 3B, turning gears 512 and 513 at the same speed in the same direction or in opposite directions will change the grip or yaw of scissors 240.

Drive shaft 514 engages an internal sector gear portion of rocker arm 540. Rocker arm 540 has a pivot 542 attached to chassis 510, so that as drive shaft 514 turns, rocker arm 540 rotates about pivot 542. Rocker arm 540 also includes protrusions (not visible in FIG. 8A) that act as pivot points for levers 550 and 560. These protrusions can be located equidistant from pivot 542, so that as rocker arm 540 rotates, one pivot moves closer to the end effector and the other pivot moves further from the end effector by an equal amount. If toothed components 520 and 530 are moved at the appropriate speeds and directions to maintain the orientations of levers 550 and 560, rotation of rocker arm 540 will pull in (or release) equal lengths of cables 571 and 572 and release (or pull in) the same lengths of cables 573 and 574. Backend mechanism 500 can thus be used to perform a pitch change as described above with reference to FIG. 3B when cables 571, 572, 573, and 574 respectively correspond to cables 251, 252, 253, and 254, but the pitch change requires coordinated rotations of all three drive shafts 512, 513, and 514. Such coordinated rotations can be implemented in software of a robotic control system.

A connector 590 and a wire 592 can be used to connect an external power supply or generator (not shown) to one or more of cables 571, 572, 573, and 574. The power supply can be of the same type currently known in monopolar cauterizing instruments, and connector 590 can be of any desired type required for connection to the particular power supply. Alternatively, connector 590 can be a standard connector type such as a banana jack that connects to the power supply through an adapter cable (not shown).

Figure 8B:
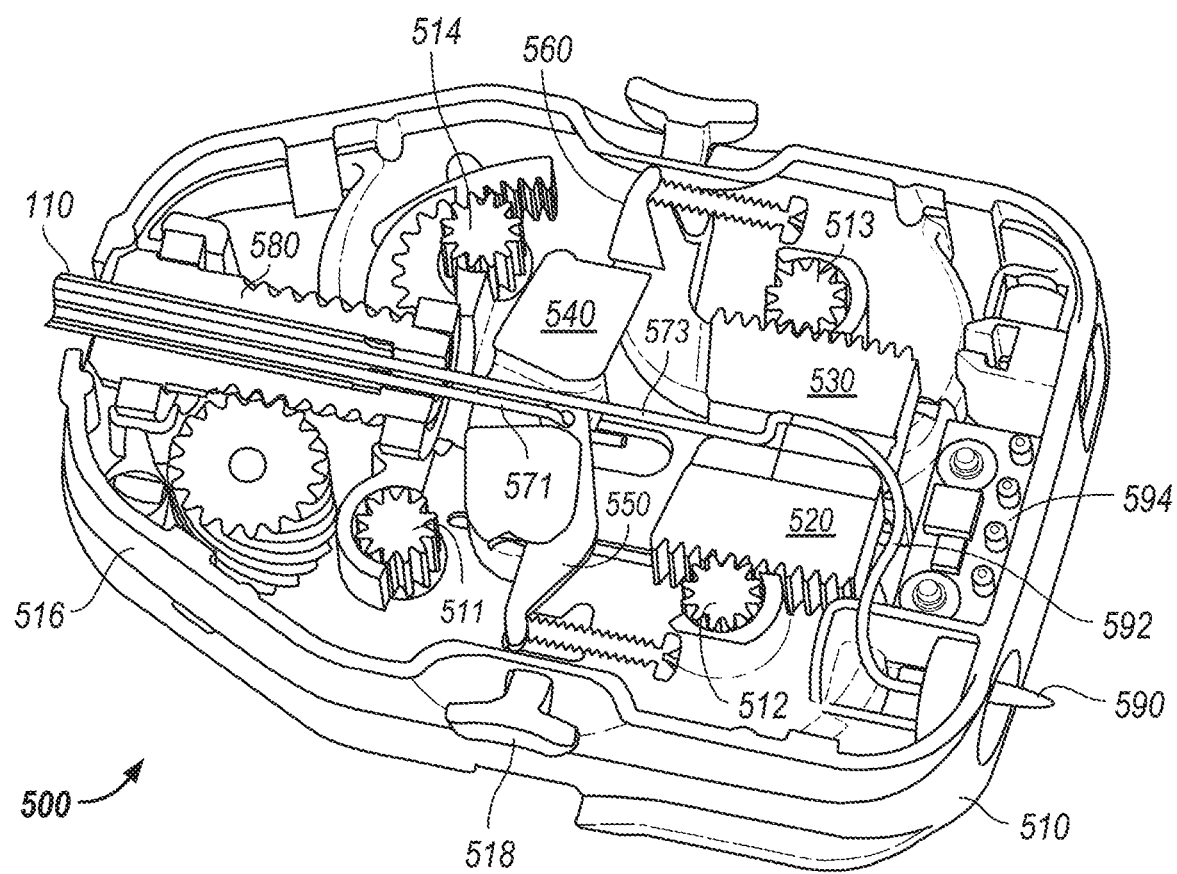

FIG. 8B shows a cross-sectional view of backend mechanism 500 when assembled with additional components not shown in FIG. 8A. As illustrated, backend mechanism 500 includes drive shafts 512, 513, and 514 that respectively engage toothed components 520, 530, and 540, and a robotic control system coupled to backend 500 can rotate drive shafts 512, 513, and 514 to control the pitch, yaw, and grip of a wrist mechanism or end effector (not shown). Cables 571, 572, 573, and 574 extend from the end effector at a distal end of a main tube 110, through main tube 110 and into backend mechanism 500. In the illustrated embodiment, wire 592 makes electrical connection to cable 573 at toothed component 530. Accordingly, wire 592 must provide sufficient slack to accommodate the range of motion of toothed component 530. Alternatively, wire 592 may be connected to any one or more of cables 571, 572, 573, and 574.

Main tube 110 is attached in backend mechanism 500 to a helical gear 580, which is coupled to a drive shaft 511 through an intervening helical gear 582. When a control system rotates drive gear 511, helical gears 582 and 580 rotate main tube 110 and thereby change the roll angle of the end effector at the distal end of main tube 110.

FIG. 8B also shows a circuit board 594, which may be included in backend mechanism 500. Circuit board 594 can provide an interface for connection to a robotic control system. Circuit board 594 would typically store information about the instrument such as an identifier identifying the type of instrument and operating parameters of the instrument such as a count of the number of uses of the instrument. In the case of a single use instrument, the control system would check and change the count of the number of uses when the instrument is used. The control system can disable uses of a single-use instrument when the use count indicates the instrument has already been used.

Backend mechanism 500 as illustrated in FIG. 8B also includes a cover 516 to enclose mechanical and electrical systems in backend mechanism 500. Cover 516 can thus isolate electrically charged cables from unintended contact. A latch system 518 can be used to lock backend mechanism in a docking port of a control system.

Figure 9A:
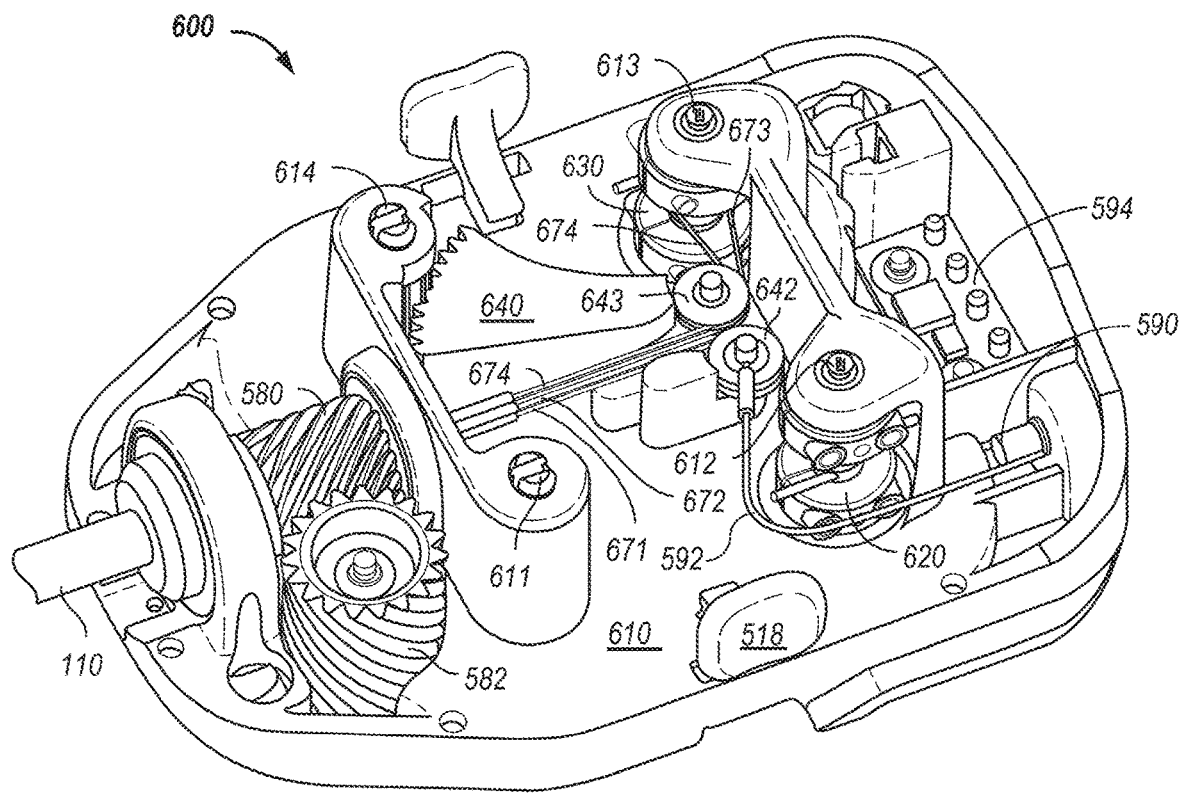
FIG. 9A shows a backend mechanism in accordance with an embodiment of the invention using pulleys, capstans, and gears to move drive cables and an electrical connection to energize at least one of the drive cables.

Pulleys and capstans can be used in a backend mechanism in place of some toothed components of FIGS. 8A and 8B. FIG. 9A shows a backend mechanism 600 in accordance with an embodiment of the invention employing cables, pulleys, and capstans. Backend mechanism 600 includes a chassis 610, four drive shafts 611, 612, 613, and 614, a pair of capstans 620 and 630, a rocker arm 640 on which pulleys 642 and 643 are mounted, helical gears 580 and 582, and electrical components 590, 592, and 594. Four drive cables 671, 672, 673, and 674, which are connected to an end effector (not shown), extend through main tube 110 into backend mechanism 600. Cables 671, 672, 673, and 674 can respectively correspond to cables 251, 252, 253, and 254, which are connected to end effector 200 of FIGS. 3A and 3B. However, backend mechanism 600 can more generally be used in any instrument for which an electrically energized drive cable and connection of four cables to three motor driven axes is desired.

The shape of chassis 610 is generally selected to have a footprint corresponding to a mounting or docking port on a robotic control system. Backend mechanism 600 may thus be fitted to a control system so that drive shafts 611, 612, 613, and 614 are mechanically coupled to motors in the control system. The control system is then able to rotate drive shafts 611, 612, 613, and 614 through precise angles that may be selected by software to achieve the desired operation or movement of the instrument.

Cables 671 and 672 pass from main tube 110, around one or more pulleys 642, and wrap around capstan 620. The wrapping of cables 671 and 672 around capstan 620 is such that when capstan 620 turns, a length of one cable 671 or 672 is pulled in and an equal length of the other cable 672 or 671 is fed out. Similarly, cables 673 and 674 pass from main tube 110, around one or more pulleys 643, and are wrapped around capstan 630, so that when capstan 630 turns, a length of one cable 673 or 674 is pulled in and an equal length of the other cable 674 or 673 fed out. Drive shafts 612 and 613 are respectively coupled to turn capstan 620 and 630. A control system can thus turn drive shafts 612 and 613 to change the yaw angle or the grip of an end effector using the processes described above. For example, when cables 671, 672, 673, and 674 respectively correspond to cables 251, 252, 253, and 254 of FIG. 3B, turning drive shafts 612 and 613 at the same speed in the same direction or in opposite directions will open, close, or change the yaw of scissors 240.

Figure 9B:
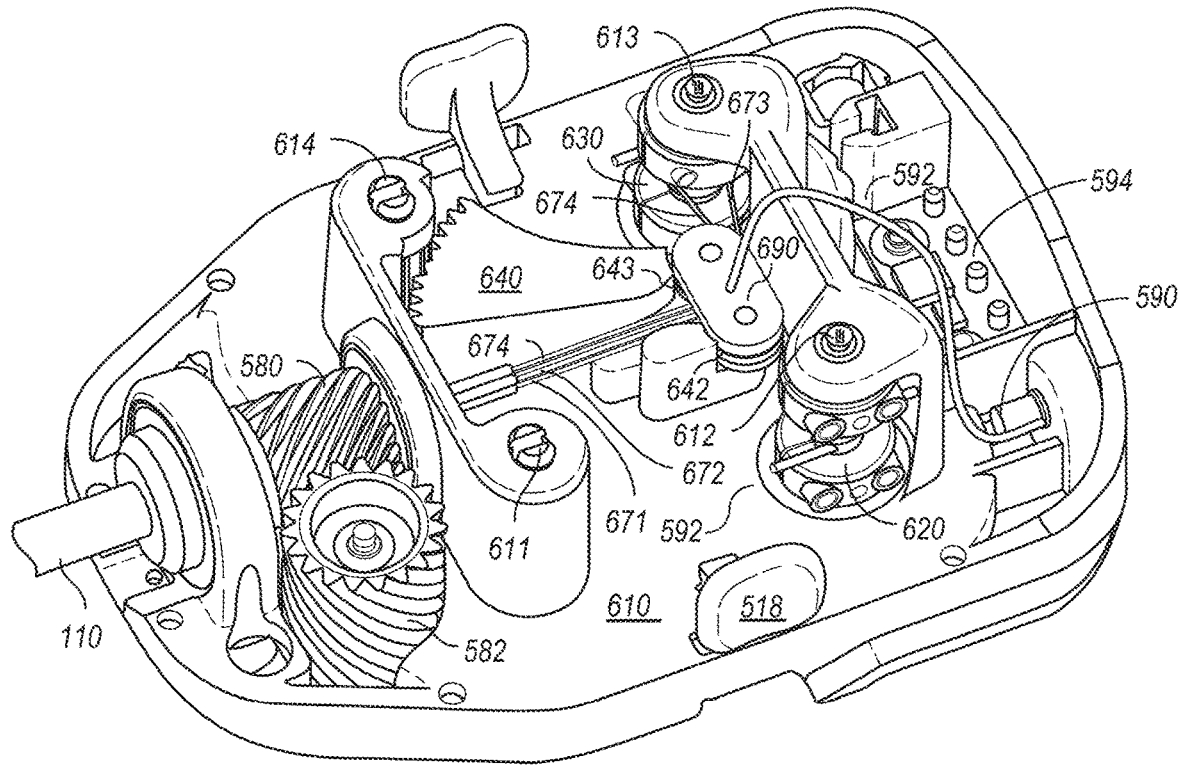
FIG. 9B shows the backend mechanism of FIG. 9A in accordance with an embodiment of the invention using a keeper to keep drive cables in their desired positions and provide electrical connections to the drive cables.

Pulleys 642 and 643 could have deep grooves, and a keeper 690 as shown in FIG. 9B could be attached to the pivot pins of pulleys 642 and 643 to help prevent electrified cables from jumping off of pulleys 642 or 643. Keeper 690 can also keep pulleys 642 and 643 from coming off their respective pins when a cable goes slack or the instrument is upside down. Pulleys 642 and 643 are mounted on rocker arm 640. Rocker arm 640 has a sector gear portion that engages drive shaft 614 and is coupled to chassis 610 to rotate about a pivot axis when drive shaft 614 turns. The sector gear portion and pivot of rocker arm 640 are designed so that rotation of rocker arm 640 primarily causes one pulley 642 or 643 to move toward its associated capstan 620 or 630 and the other pulley 643 or 642 to move away from its associated capstan 630 or 620. This effectively pulls in lengths of one pair of cables 671 and 672 or 673 and 674 and releases an equal length of the other pair of cables 673 and 674 or 671 and 672. Backend mechanism 600 simply through rotation of drive shaft 614 can thus change the pitch in an end effector as described above with reference to FIG. 3B when cables 671, 672, 673, and 674 respectively correspond to cables 251, 252, 253, and 254.

Backend mechanism 600 can control the roll angle of a wrist mechanism at the distal end of main tube 110 using drive shaft 611 to turn helical gears 582 and 580, which are coupled to main tube 110 in the same manner as described above.

Cables 671, 672, 673, and 674 in backend mechanism 600 wind or wrap around pulleys 642 and 643 and capstans 620 and 630 and must be able to flex when capstans 620 and 630 rotate. Accordingly, portions of cables 671, 672, 673, and 674 in backend mechanism 600 require flexibility and may be, for example, stranded metal cable that can be flexed repeatedly around relatively sharp turns without damage. Accordingly, each cable 671, 672, 673, and 674 may include three portions, a stranded cable portion at the end effector, a more rigid portion (e.g., a hypotube) extending through the straight portion of main tube 110, and a second stranded cable portion in backend mechanism 600. For comparison, backend mechanism 500 of FIG. 8B moves cables 571, 572, 573, and 574 in nearly linear motions and does not require significant flexing of cables 571, 572, 573, and 574 around pulleys or other sharp bends. Accordingly, the portions of cables 571, 572, 573, and 574 in backend mechanism 500 can be relatively rigid structures such as hypotubes.

Wire 592 and electrical connector 590, which can be used for connection of a power supply or generator as described above, is connected to the hub or pivot pin of pulleys 642 in the illustrated embodiment of FIG. 9A. Alternatively, electrical connections to the pivot pins of pulleys 642 and 643 can be made through keeper 690 which contacts the pivot pins. Pulleys 642 and 643 and the pivot pins can be made of an electrically conductive material such as metal, so that one or more the metal cables 671, 672, 673, and 674 are electrically energized when wire 592 is electrically energized. Since pulleys 642 and 643 and keeper 690 move when rocker arm 640 rotates, wire 592 requires sufficient slack to accommodate the range of motion. Backend mechanism 600 of FIG. 9A or 9B like backend mechanism 500 of FIG. 8B also includes a circuit board 594 with circuits and connectors for electrical systems that may be employed in a medical instrument that connects to a robotic control system.

Embodiments of the invention as described above can reduce the number of components in an electrified medical instrument and thereby reduce costs through use of drive cables as electrical conductors. Reduction of the cost has obvious benefits, but also enables the creation of single-use instruments that are cost competitive (per case) when compared to existing reusable instruments. A single-use instrument has further benefits of eliminating reprocessing and sterilization at the hospital and allows further cost savings during manufacture of the instruments because components do not need to be designed and verified to enable reprocessing. Additionally, disposable scissors will ensure the cutting blades are new and sharp.

Although the invention has been described with reference to particular embodiments, the description is only an example of the invention's application and should not be taken as a limitation. In particular, although the above description concentrated on embodiments of the invention that are monopolar scissors, aspects of the invention can be employed in other electrically energized medical instruments such as instruments having non-gripping end effectors such as wire loops or scalpels or having general electrodes with hook shapes, spatula shapes, ball-end shapes, needle shapes, or other shapes. A gripping end effector such as forceps could also be energized to provide an instrument that is usable to grasp tissue and/or apply monopolar cautery energy. Various other adaptations and combinations of features of the embodiments disclosed are within the scope of the invention as defined by the following claims.

What is claimed is:

1. An apparatus, comprising:
a shaft comprising a distal end portion and a proximal end portion;
a wrist mechanism comprising a distal portion movably coupled to a proximal portion, the wrist mechanism coupled to the distal end portion of the shaft, and the wrist mechanism defining a wrist portion of a cable path;
an end effector coupled to the distal portion of the wrist mechanism, actuation of the end effector producing movement of the end effector relative to the distal portion of the wrist mechanism;
a cable pair routed through the wrist portion of the cable path, a first portion of the cable pair being coupled to the end effector; and
a transmission coupled to a portion of the shaft, the transmission comprising a drive shaft and a rocker arm,
the transmission defining a transmission portion of the cable path between the drive shaft and the shaft, the cable pair being routed through the transmission portion of the cable path,
the drive shaft being configured to move a portion of the cable pair to actuate the end effector,
the rocker arm coupled to a pulley in contact with the cable pair, the rocker arm configured to move the pulley to change a length of the transmission portion of the cable path.

2. The apparatus of claim 1, wherein the rocker arm comprises a first arm portion with the pulley mounted thereon, the pulley defining a portion of the transmission portion of the cable path.

3. The apparatus of claim 2, wherein rotation of the first arm portion causes the pulley to move relative to the drive shaft.

4. The apparatus of claim 2, wherein the pulley is a first pulley, the cable pair is a first cable pair, the cable path is a first cable path,
the rocker arm further comprises a second arm portion,
the transmission comprises a second pulley mounted on the second arm portion of the rocker arm,
the transmission defining a transmission portion of a second cable path between a second drive shaft and the shaft, and
a second cable pair is in contact with the second pulley, the second cable pair being routed along the transmission portion of the second cable path.

5. The apparatus of claim 4, wherein the rocker arm is configured to move the first pulley and the second pulley to lengthen the transmission portion of the first cable path while shortening the transmission portion of the second cable path.

6. The apparatus of claim 5, wherein the first arm portion and the second arm portion are operatively connected such that the first arm portion and the second arm portion rotate together.

7. The apparatus of claim 4, wherein the first arm portion and the second arm portion are between the drive shaft and the proximal end portion of the shaft.

8. The apparatus of claim 1, wherein:
the drive shaft is operatively coupled to a second portion of the cable pair and configured to move the second portion of the cable pair, and
the pulley rotates between a first position relative to the drive shaft and a second position relative to the drive shaft to change the length of the transmission portion of the cable path, wherein the pulley is closer to the drive shaft in the first position than in the second position.

9. The apparatus of claim 8, wherein the cable path is a first cable path, the cable pair is a first cable pair, and the transmission further comprises a transmission portion of a second cable path, and
a second cable pair is routed through the transmission portion of the second cable path, and in contact with a second pulley,
the rocker arm is configured to move the second pulley to lengthen the transmission portion of the first cable path while shortening the transmission portion of the second cable path.

10. The apparatus of claim 1, wherein the pulley is a first pulley, and the transmission further comprises a second pulley in contact with a second cable pair, the first pulley is mounted on a first arm portion of the rocker arm, and the second pulley that is mounted on a second arm portion of the rocker arm.

11. The apparatus of claim 10, wherein the first arm portion and the second arm portion are operatively connected such that the first arm portion and the second arm portion rotate together.

12. The apparatus of claim 1, wherein the cable path is a first cable path, the cable pair is a first cable pair, the pulley is a first pulley, the drive shaft is a first drive shaft, and the transmission further comprises a second pulley, a second drive shaft, and defines a transmission portion of a second cable path between the second drive shaft and the shaft, the apparatus further comprising:
a second cable pair routed through the transmission portion of the second cable path, and in contact with the second pulley, and
the rocker arm is configured to move the first pulley closer to the first drive shaft to lengthen the transmission portion of the first cable path while shortening the length of the transmission portion of the second cable path.

13. The apparatus of claim 1, wherein the cable path is a first cable path, the cable pair is a first cable pair, the pulley is a first pulley, the drive shaft is a first drive shaft, and the transmission further comprises a second pulley, a second drive shaft, and defines a transmission portion of a second cable path between the second drive shaft and the shaft, the apparatus further comprising:
a second cable pair routed through the transmission portion of the second cable path, and in contact with the second pulley, and the rocker arm is configured to move the second pulley closer to the second drive shaft to lengthen the transmission portion of the second cable path while shortening the length of the transmission portion of the first cable path.

* * * * *